US010011881B2

(12) United States Patent
Furihata et al.

(10) Patent No.: US 10,011,881 B2
(45) Date of Patent: Jul. 3, 2018

(54) ALTERNATIVE SPLICING VARIANT OF OATP1B3 MRNA

(71) Applicant: National University Corporation Chiba University, Chiba-shi (JP)

(72) Inventors: Tomomi Furihata, Chiba (JP); Sayaka Matsumoto, Chiba (JP); Miki Nagai, Chiba (JP); Kan Chiba, Chiba (JP)

(73) Assignee: National University Corporation China University, Chiba (JP)

( * ) Notice: Subject to any disclaimer, the term of this patent is extended or adjusted under 35 U.S.C. 154(b) by 0 days.

(21) Appl. No.: 15/226,278

(22) Filed: Aug. 2, 2016

(65) Prior Publication Data

US 2016/0333426 A1 Nov. 17, 2016

Related U.S. Application Data

(62) Division of application No. 13/030,485, filed on Feb. 18, 2011, now Pat. No. 9,404,158.

(30) Foreign Application Priority Data

Feb. 19, 2010 (JP) ................................ 2010-035166
Feb. 17, 2011 (JP) ................................ 2011-032501

(51) Int. Cl.

| | |
|---|---|
| ***C07H 21/04*** | (2006.01) |
| ***C12Q 1/68*** | (2018.01) |
| ***C12Q 1/6886*** | (2018.01) |
| ***C07K 14/47*** | (2006.01) |
| ***G01N 33/50*** | (2006.01) |
| *A61K 39/00* | (2006.01) |

(52) U.S. Cl.

CPC ........ *C12Q 1/6886* (2013.01); *C07K 14/4748* (2013.01); *G01N 33/5011* (2013.01); *A61K 39/00* (2013.01); *C07K 2319/21* (2013.01); *C07K 2319/41* (2013.01); *C07K 2319/42* (2013.01); *C07K 2319/43* (2013.01); *C07K 2319/60* (2013.01); *C12Q 2600/136* (2013.01); *C12Q 2600/156* (2013.01); *C12Q 2600/158* (2013.01)

(58) Field of Classification Search

None

See application file for complete search history.

(56) References Cited

U.S. PATENT DOCUMENTS

| | | | |
|---|---|---|---|
| 6,964,868 | B1 | 11/2005 | Williams et al. |
| 7,618,814 | B2 | 11/2009 | Bentwich |
| 7,745,391 | B2 | 1/2010 | Mintz et al. |
| 2001/0053519 | A1 | 12/2001 | Fodor et al. |

FOREIGN PATENT DOCUMENTS

| | | |
|---|---|---|
| JP | 2007-119390 | 5/2007 |

OTHER PUBLICATIONS

Nagai et al. (Drug Metabolism Reviews, vol. 42, Supp 1, pp. 32-33, Aug. 2010).*

Vandenbroucke (Nucleic Acids Research, vol. 29, No. 13, e68, 2001).*

Imai et al. (Pharm Res, vol. 30, pp. 2880-2890, 2013).*

Thakkar et al. (Molecular Pharmaceutics, vol. 10, pp. 406-416, Dec. 8, 2012).*

Kindla et al. (Cancer Biology & Therapy, vol. 11, No. 6, pp. 584-591, 2011).*

Nagai et al. (Biochemical and Biophysical Research Communications, vol. 418, pp. 818-823, 2012).*

Briz et al "Role of Organic Anion-Transporting Polypeptides, OATP-A, OATP-C and OATP-B, in the Human Placenta-Maternal Liver Tandem Excretory Pathway for Foetal Bilirubin" Biochemical Journal vol. 371, pp. 897-905, 2003.

Furihata et al "Identification of a Cancer-Cell Specific Splicing Isoform of Organic Anion Transporting Polypeptide 1B3" Abstracts of the 83$^{rd}$ Meeting of the Japanese Biochemical Society, 2010.

Hamada et al "Effect of SLCO1B3 Haplotype on Testosterone Transport and Clinical Outcome in Caucasian Patients with Androgen-Independent Prostatic Cancer" Clinical Cancer Research vol. 14, pp. 3312-3318, 2008.

Imai et al "Epigenetic Regulation of Organic Anion Transporting Polypeptide IB3 in Cancer Cell Lines" Pharmaceutical Research vol. 30, pp. 2880-2890, 2013.

Ishii et al "A Novel mRNA Splicing Isoform is a Real Cancer-Type Organic Anion Transporting Polypeptide 1B3 mRNA" Abstracts of the 25$^{th}$ Annual Meeting of the Japanese Society for the Study of Xenobiotics, 2010.

Kindla et al "Expression and Localization of the Uptake Transporters OATP2B1, OATP3A1 and OATP5A1 in Non-Malignant and Malignant Breast Tissue" Cancer Biology & Therapy vol. 11, pp. 584-591, 2011.

Lee et al "Overexpression of OATP1B3 Confers Apoptotic Resistance in Colon Cancer" Cancer Research vol. 68, pp. 10315-10323, 2008.

(Continued)

*Primary Examiner* — Jeanine A Goldberg

(74) *Attorney, Agent, or Firm* — Cesari and McKenna, LLP

(57) ABSTRACT

[PROBLEM TO BE SOLVED]

An object of the present invention is to provide a novel tumor marker and use thereof. In more detail, the present invention provides a novel tumor marker, a method for measuring said tumor marker and a measurement kit, a method for detecting cancer using the same, a kit for detecting cancer, a method for screening a preventive and/or therapeutic agent for cancer, as well as a medicament such as cancer vaccine.

[SOLUTION]

According to the present invention, a method for measuring an alternative splicing variant of OATP1B3 mRNA in a sample to be examined is provided. Said measurement method comprises measuring mRNA comprising a nucleotide sequence represented by SEQ ID NO: 1 in the sequence listing table in a sample to be examined isolated from living organism with differentiation from a mRNA comprising a nucleotide sequence represented by SEQ ID NO: 2. Said measurement method is useful for detecting cancer or screening a preventive and/or therapeutic agent.

6 Claims, 8 Drawing Sheets

(56) References Cited

OTHER PUBLICATIONS

Mahagita et al "Human Organic Anion Transporter 1B1 and 1B3 Function as Bidirectional Carriers and Do Not Mediate GSH-Bile Acid Cotransport" American Journal of Physiology Gastrointestinal and Liver Physiology vol. 293, pp. G271-G278, 2007.
Matsumoto et al "Identification of Cancer-Type OATP1B3 Expressed in Cancer Cells" Proceedings of the 130$^{th}$ Annual Meeting of the Pharmaceutical Society of Japan vol. 130, p. 108, 2010.
Muto et al "Human Liver-Specific Organic Anion Transporter-2 is a Potent Prognostic Factor for Human Breast Carcinoma" Cancer Science vol. 98, pp. 1570-1576, 2007.
Nagai et al "A Novel mRNA Splicing Isoform is a Real Cancer-Type Organic Anion Transporting Polypeptide IB3 mRNA" Drug Metabolism Reviews vol. 42, pp. 32-33, 2010.
Nagai et al "Identification of a New Organic Anion Transporting Polypeptide 1B3 mRNA Isoform Primarily Expressed in Human Cancerous Tissues and Cells" Biochemical and Biophysical Research Communications vol. 418, pp. 818-823, 2012.
Thakkar et al "A Cancer-Specific Variant of the SLCO1B3 Gene Encodes a Novel Human Organic Anion Transporting Polypeptide 1B3 (OATP1B3) Localized Mainly in the Cytoplasm of Colon and Pancreatic Cancer Cells" Molecular Pharmaceutics vol. 10, pp. 406-416, 2013.
Vandenbroucke et al "Quantification of Splice Variants Using Real-Time PCR" Nucleic Acids Research vol. 29, pp. 1-7, 2001.

* cited by examiner

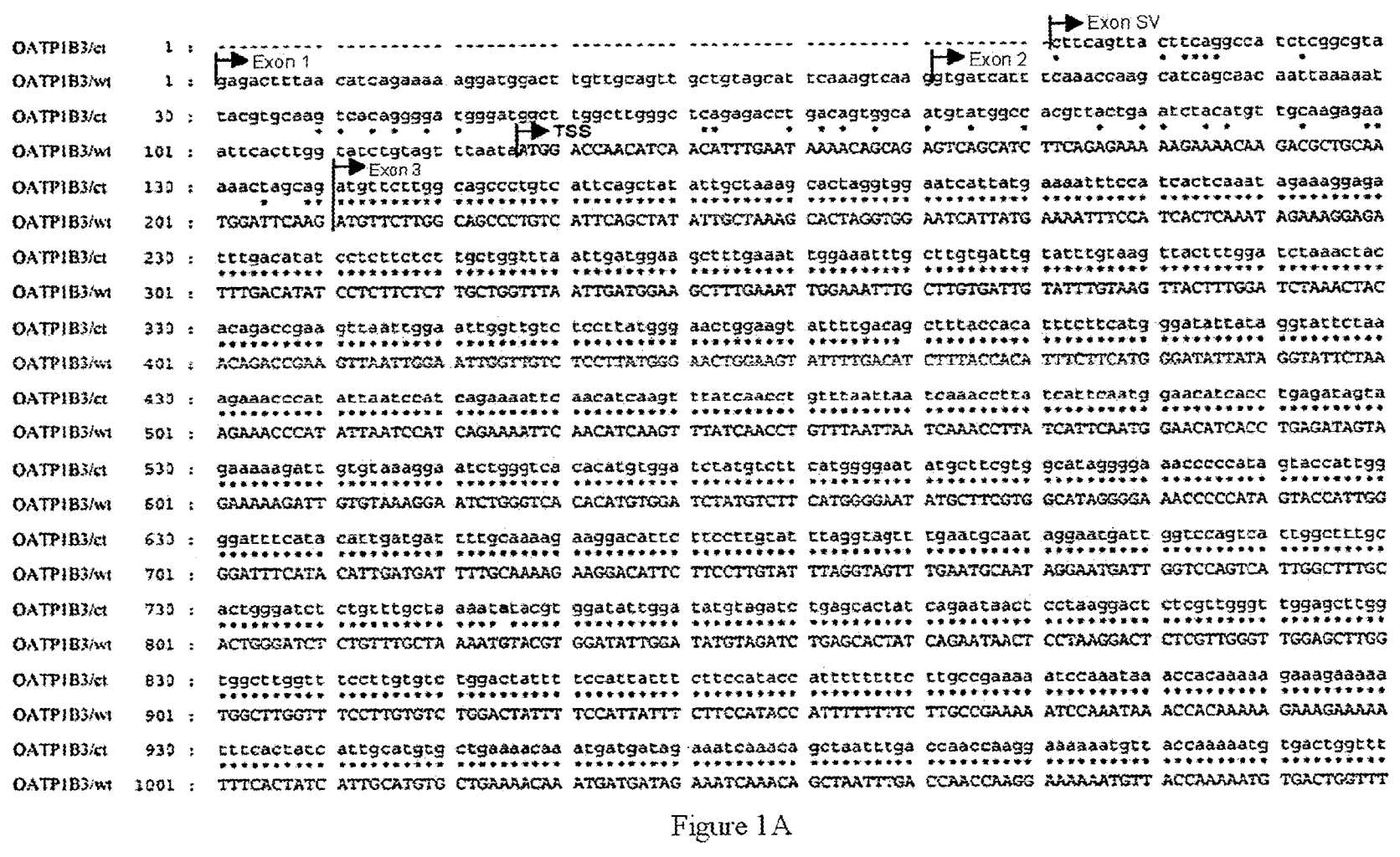

```
                                                                                                Exon SV
OATP1B3/ct    1 : ---------- ---------- ---------- ---------- ---------- ---------- ---------- -cttcagtta cttcaggcca tctcggcgta
                  Exon 1                                                              Exon 2
OATP1B3/wt    1 : gagactttaa catcagaaaa aggatggact tgttgcagtt gctgtagcat tcaaagtcaa ggtgatcatt tcaaaccaag catcagcaac aattaaaaat

OATP1B3/ct   30 : tacgtgcaag tcacagggga tgggatggct tggcttgggc tcagagacct gacagtggca atgtatggcc acgttactga atctacatgt tgcaagagaa
                                              TSS
OATP1B3/wt  101 : attcacttgg tatctgtagt ttaataATGG ACCAACATCA ACATTTGAAT AAAACAGCAG AGTCAGCATC TTCAGAGAAA AAGAAAACAA GACGCTGCAA
                             Exon 3
OATP1B3/ct  130 : aaactagcag atgttcttgg cagccctgtc attcagctat attgctaaag cactaggtgg aatcattatg aaaatttcca tcactcaaat agaaaggaga

OATP1B3/wt  201 : TGGATTCAAG ATGTTCTTGG CAGCCCTGTC ATTCAGCTAT ATTGCTAAAG CACTAGGTGG AATCATTATG AAAATTTCCA TCACTCAAAT AGAAAGGAGA

OATP1B3/ct  230 : tttgacatat cctcttctct tgctggttta attgatggaa gctttgaaat tggaaatttg cttgtgattg tatttgtaag ttactttgga tctaaactac

OATP1B3/wt  301 : TTTGACATAT CCTCTTCTCT TGCTGGTTTA ATTGATGGAA GCTTTGAAAT TGGAAATTTG CTTGTGATTG TATTTGTAAG TTACTTTGGA TCTAAACTAC

OATP1B3/ct  330 : acagaccgaa gttaattgga attggttgtc tccttatggg aactggaagt attttgacag ctttaccaca tttcttcatg ggatattata ggtattctaa

OATP1B3/wt  401 : ACAGACCGAA GTTAATTGGA ATTGGTTGTC TCCTTATGGG AACTGGAAGT ATTTTGACAT CTTTACCACA TTTCTTCATG GGATATTATA GGTATTCTAA

OATP1B3/ct  430 : agaaacccat attaatccat cagaaaattc aacatcaagt ttatcaacct gtttaattaa tcaaacctta tcattcaatg gaacatcacc tgagatagta

OATP1B3/wt  501 : AGAAACCCAT ATTAATCCAT CAGAAAATTC AACATCAAGT TTATCAACCT GTTTAATTAA TCAAACCTTA TCATTCAATG GAACATCACC TGAGATAGTA

OATP1B3/ct  530 : gaaaaagatt gtgtaaagga atctgggtca cacatgtgga tctatgtctt catggggaat atgcttcgtg gcatagggga aacccccata gtaccattgg

OATP1B3/wt  601 : GAAAAAGATT GTGTAAAGGA ATCTGGGTCA CACATGTGGA TCTATGTCTT CATGGGGAAT ATGCTTCGTG GCATAGGGGA AACCCCCATA GTACCATTGG

OATP1B3/ct  630 : ggatttcata cattgatgat tttgcaaaag aaggacattc ttccttgtat ttaggtagtt tgaatgcaat aggaatgatt ggtccagtca ttggctttgc

OATP1B3/wt  701 : GGATTTCATA CATTGATGAT TTTGCAAAAG AAGGACATTC TTCCTTGTAT TTAGGTAGTT TGAATGCAAT AGGAATGATT GGTCCAGTCA TTGGCTTTGC

OATP1B3/ct  730 : actgggatct ctgtttgcta aaatatacgt ggatattgga tatgtagatc tgagcactat cagaataact cctaaggact ctcgttgggt tggagcttgg

OATP1B3/wt  801 : ACTGGGATCT CTGTTTGCTA AAATGTACGT GGATATTGGA TATGTAGATC TGAGCACTAT CAGAATAACT CCTAAGGACT CTCGTTGGGT TGGAGCTTGG

OATP1B3/ct  830 : tggcttggtt tccttgtgtc tggactattt tccattattt cttccatacc atttttttc ttgccgaaaa atccaaataa accacaaaaa gaaagaaaaa

OATP1B3/wt  901 : TGGCTTGGTT TCCTTGTGTC TGGACTATTT TCCATTATTT CTTCCATACC ATTTTTTTTC TTGCCGAAAA ATCCAAATAA ACCACAAAAA GAAAGAAAAA

OATP1B3/ct  930 : tttcactatc attgcatgtg ctgaaaacaa atgatgatag aaatcaaaca gctaatttga ccaaccaagg aaaaaatgtt accaaaaatg tgactggttt

OATP1B3/wt 1001 : TTTCACTATC ATTGCATGTG CTGAAAACAA ATGATGATAG AAATCAAACA GCTAATTTGA CCAACCAAGG AAAAAATGTT ACCAAAAATG TGACTGGTTT
```

Figure 1A

```
OATP1B3/ct   1030 :  tttccagtct ttgaaaagca tccttaccaa tcccctgtat gttatatttc tgcttttgac attgttacaa gtaagcagct ttattggttc ttttacttac
                     ********** ********** ********** ********** ********** ********** ********** ********** ********** **********
OATP1B3/wt   1101 :  TTTCCAGTCT TTGAAAAGCA TCCTTACCAA TCCCCTGTAT GTTATATTTC TGCTTTTGAC ATTGTTACAA GTAAGCAGCT TTATTGGTTC TTTTACTTAC

OATP1B3/ct   1130 :  gtctttaaat atatggagca acagtacggt cagtctgcat ctcatgctaa cttttttgttg ggaatcataa ccattcctac ggttgcaact ggaatgtttt
                     ********** ********** ********** ********** ********** ********** ********** ********** ********** **********
OATP1B3/wt   1201 :  GTCTTTAAAT ATATGGAGCA ACAGTACGGT CAGTCTGCAT CTCATGCTAA CTTTTTGTTG GGAATCATAA CCATTCCTAC GGTTGCAACT GGAATGTTTT

OATP1B3/ct   1230 :  taggaggatt tatcattaaa aaattcaaat tgtctttagt tggaattgcc aaatttttcat ttcttacttc gatgatatcc ttcttgtttc aacttctata
                     ********** ********** ********** ********** ********** ********** ********** ********** ********** **********
OATP1B3/wt   1301 :  TAGGAGGATT TATCATTAAA AAATTCAAAT TGTCTTTAGT TGGAATTGCC AAATTTTCAT TTCTTACTTC GATGATATCC TTCTTGTTTC AACTTCTATA

OATP1B3/ct   1330 :  tttccctcta atctgcgaaa gcaaatcagt tgccggccta accttgacct atgatggaaa taattcagtg gcatctcatg tagatgtacc actttcttat
                     ********** ********** ********** ********** ********** ********** ********** ********** ********** **********
OATP1B3/wt   1401 :  TTTCCCTCTA ATCTGCGAAA GCAAATCAGT TGCCGGCCTA ACCTTGACCT ATGATGGAAA TAATTCAGTG GCATCTCATG TAGATGTACC ACTTTCTTAT

OATP1B3/ct   1430 :  tgcaactcag agtgcaattg tgatgaaagt cagtgggaac cagtctgtgg gaacaatgga ataacttacc tgtcaccttg tttagcagga tgcaaatcct
                     ********** ********** ********** ********** ********** ********** ********** ********** * ******** **********
OATP1B3/wt   1501 :  TGCAACTCAG AGTGCAATTG TGATGAAAGT CAGTGGGAAC CAGTCTGTGG GAACAATGGA ATAACTTACC TGTCACCTTG TCTAGCAGGA TGCAAATCCT

OATP1B3/ct   1530 :  caagtggtat taaaaagcat acagtgtttt ataactgtag ttgtgtggaa gtaactggtc tccagaacag aaattactca gcgcacttgg gtgaatgccc
                     ********** ********** ********** ********** ********** ********** ********** ********** ** ******* **********
OATP1B3/wt   1601 :  CAAGTGGTAT TAAAAAGCAT ACAGTGTTTT ATAACTGTAG TTGTGTGGAA GTAACTGGTC TCCAGAACAG AAATTACTCA GCACACTTGG GTGAATGCCC

OATP1B3/ct   1630 :  aagagataat acttgtacaa ggaaattttt catctatgtt gcaattcaag tcataaactc tttgttctct gcaacaggag gtaccacatt tatcttgttg
                     ********** ********** ********** ********** ********** ********** ********** ********** ********** **********
OATP1B3/wt   1701 :  AAGAGATAAT ACTTGTACAA GGAAATTTTT CATCTATGTT GCAATTCAAG TCATAAACTC TTTGTTCTCT GCAACAGGAG GTACCACATT TATCTTGTTG

OATP1B3/ct   1730 :  actgtgaaga ttgttcaacc tgaattgaaa gcacttgcaa tgggtttcca gtcaatggtt ataagaacac taggaggaat tctagctcca atatattttg
                     ********** ********** ********** ********** ********** ********** ********** ********** ********** **********
OATP1B3/wt   1801 :  ACTGTGAAGA TTGTTCAACC TGAATTGAAA GCACTTGCAA TGGGTTTCCA GTCAATGGTT ATAAGAACAC TAGGAGGAAT TCTAGCTCCA ATATATTTTG

OATP1B3/ct   1830 :  gggctctgat tgataaaaca tgtatgaagt ggtccaccaa cagctgtgga gcacaaggag cttgtaggat atataattcc gtattttttg gaagggtcta
                     ********** ********** ********** ********** ********** ******** * ********** ********** ********** **********
OATP1B3/wt   1901 :  GGGCTCTGAT TGATAAAACA TGTATGAAGT GGTCCACCAA CAGCTGTGGA GCACAAGGGG CTTGTAGGAT ATATAATTCC GTATTTTTTG GAAGGGTCTA

OATP1B3/ct   1930 :  cttgggctta tctatagctt taagattccc agcacttgtt ttatatattg ttttcatttt tgctatgaag aaaaaatttc aaggaaaaga taccaaggca
                     ********** ********** ********** ********** ********** ********** ********** ********** ********** **********
OATP1B3/wt   2001 :  CTTGGGCTTA TCTATAGCTT TAAGATTCCC AGCACTTGTT TTATATATTG TTTTCATTTT TGCTATGAAG AAAAAATTTC AAGGAAAAGA TACCAAGGCA
```

Figure 1B

```
OATP1B3/ct   2030 : tcggacaatg aaagaaaagt aatggatgaa gcaaacttag aattcttaaa taatggtgaa cattttgtac cttctgctgg aacagatagt aaaacatgta
                    ********** ********** ********** ********** ********** ********** ********** ********** ********** **********
OATP1B3/wt   2101 : TCGGACAATG AAAGAAAAGT AATGGATGAA GCAAACTTAG AATTCTTAAA TAATGGTGAA CATTTTGTAC CTTCTGCTGG AACAGATAGT AAAACATGTA
OATP1B3/ct   2130 : atttggacat gcaagacaat gctgctgcca actaacattg c--------- ---------- ---------- ---------- ---------- ----------
                    ********** ********** ********** ********** *
OATP1B3/wt   2201 : ATTTGGACAT GCAAGACAAT GCTGCTGCCA ACTAAcattg cattgattca ttaagatgtt attttgagg tgttcctggt ctttcactga caattccaac
OATP1B3/ct   2163 : ---------- ---------- ---------- ---------- ---------- ---------- ---------- ---------- ---------- ----------
OATP1B3/wt   2301 : attctttact tacagtggac caatggataa gtctatgcat ctataataaa ctataaaaaa tgggagtacc catggttagg atatagctat gcctttatgg
OATP1B3/ct   2163 : ---------- ---------- ---------- ---------- ---------- ---------- ---------- ---------- ---------- ----------
OATP1B3/wt   2401 : ttaagattag aatatatgat ccataaaaat ttaaagtgag aggcatggtt agtgtgtgat acaataaaaa gtaattgttt ggtagttgta actgctaata
OATP1B3/ct   2163 : ---------- ---------- ---------- ---------- ---------- ---------- ---------- ---------- ---------- ----------
OATP1B3/wt   2501 : aaaccagtga ctagaatata agggaggtaa aaaggacaag atagattaat agcctaaata aagagaaaag cctgatgcct ttaaaaaaaa tgaaacactt
OATP1B3/ct   2163 : ---------- ---------- ---------- ---------- ---------- ---------- ---------- ---------- ---------- ----------
OATP1B3/wt   2601 : tggatgtatt acttaggcca aaatctggcc tggatttatg ctataatata tattttcatg ttaagttgta tatttttcag aaattataaa tattattaat
OATP1B3/ct   2163 : ---------- --
OATP1B3/wt   2701 : ttaaaatttg aa
```

Frame 1-1
GGGATGGGATGGCTTGGCTTGGGCTCAGAGACC TGA
M G W L G L G S E T ^ *
GFP

Frame 1-2
GTGCAAGTCACAGGGGATGGGATGGCTTGGCTTGGGCTCAGAGACCTGACAGTGGCAATGTATGGCCACGTTACTGAATCTACATGTTGCAAGAGAAAAACTAGCAGATGTTCTTGGCAGCCCTGTCATTCAGCTATATTGC TAA
M A T L L N L H V A R E K L A D
V L G S P V I Q L Y C ^ *
GFP Frame 2
GTGCAAGTCACAGGGGATGGGATGGCTTGGCTTGGGCTCAGAGACCTGACAGTGGCAATGTATGGCCACGTTACTGAATCTACATGTTGCAAGAGAAAAACTAGCAGATGTTCTTGGCAGCCCTGTCATTCAGCTATATTGCTAAAGCACTAGGTGGAATCATTATGAAAATTTCCATCACTCAAATAGAAAGGAGATTTGACATATCCTCTTCTCTTGCTGGT TGA
M K I S I T Q I E R R F D I S S S L A
G ^ *
GFP Frame 3
GTGCAAGTCACAGGGGATGGGATGGCTTGGCTTGGGCTCAGAGACCTGACAGTGGCAATGTATGGCCACGTTACTGAATCTACATGTTGCAAGAGAAAAACTAGCAGATGTTCTTGGCAGCCCTGTCATTCAGCTATATTGCTAAAGCAC TAG
M A W L G L R D L T V
A M Y G H V T E S T C C K R K T S R
C S W Q P C H S A I L L K H ^ *
GFP

SEQUENCE LISTING

```
<160> NUMBER OF SEQ ID NOS: 32

<210> SEQ ID NO 1
<211> LENGTH: 2169
<212> TYPE: DNA
<213> ORGANISM: Homo sapiens

<400> SEQUENCE: 1

cttcagttac ttcaggccat ctcggcgtat acgtgcaagt cacaggggat gggatggctt     60

ggcttgggct cagagacctg acagtggcaa tgtatggcca cgttactgaa tctacatgtt    120

gcaagagaaa aactagcaga tgttcttggc agccctgtca ttcagctata ttgctaaagc    180

actaggtgga atcattatga aaatttccat cactcaaata gaaaggagat ttgacatatc    240

ctcttctctt gctggtttaa ttgatggaag ctttgaaatt ggaaatttgc ttgtgattgt    300

atttgtaagt tactttggat ctaaactaca cagaccgaag ttaattggaa ttggttgtct    360

ccttatggga actggaagta ttttgacagc tttaccacat ttcttcatgg gatattatag    420

gtattctaaa gaaacccata ttaatccatc agaaaattca acatcaagtt tatcaacctg    480

tttaattaat caaaccttat cattcaatgg aacatcacct gagatagtag aaaaagattg    540

tgtaaaggaa tctgggtcac acatgtggat ctatgtcttc atggggaata tgcttcgtgg    600

cataggggaa acccccatag taccattggg gatttcatac attgatgatt ttgcaaaaga    660

aggacattct tccttgtatt taggtagttt gaatgcaata ggaatgattg gtccagtcat    720

tggctttgca ctgggatctc tgtttgctaa aatatacgtg gatattggat atgtagatct    780

gagcactatc agaataactc ctaaggactc tcgttgggtt ggagcttggt ggcttggttt    840

ccttgtgtct ggactatttt ccattatttc ttccatacca ttttttttct tgccgaaaaa    900

tccaaataaa ccacaaaaag aaagaaaaat ttcactatca ttgcatgtgc tgaaaacaaa    960

tgatgataga aatcaaacag ctaatttgac caaccaagga aaaaatgtta ccaaaaatgt   1020
```

```
gactggtttt ttccagtctt tgaaaagcat ccttaccaat cccctgtatg ttatatttct   1080

gcttttgaca ttgttacaag taagcagctt tattggttct tttacttacg tctttaaata   1140

tatggagcaa cagtacggtc agtctgcatc tcatgctaac tttttgttgg gaatcataac   1200

cattcctacg gttgcaactg gaatgttttt aggaggattt atcattaaaa aattcaaatt   1260

gtctttagtt ggaattgcca aattttcatt tcttacttcg atgatatcct tcttgtttca   1320

acttctatat ttccctctaa tctgcgaaag caaatcagtt gccggcctaa ccttgaccta   1380

tgatggaaat aattcagtgg catctcatgt agatgtacca ctttcttatt gcaactcaga   1440

gtgcaattgt gatgaaagtc agtgggaacc agtctgtggg aacaatggaa taacttacct   1500

gtcaccttgt ttagcaggat gcaaatcctc aagtggtatt aaaaagcata cagtgtttta   1560

taactgtagt tgtgtggaag taactggtct ccagaacaga aattactcag cgcacttggg   1620

tgaatgccca agagataata cttgtacaag gaaatttttc atctatgttg caattcaagt   1680

cataaactct ttgttctctg caacaggagg taccacattt atcttgttga ctgtgaagat   1740

tgttcaacct gaattgaaag cacttgcaat gggtttccag tcaatggtta taagaacact   1800

aggaggaatt ctagctccaa tatattttgg ggctctgatt gataaaacat gtatgaagtg   1860

gtccaccaac agctgtggag cacaaggagc ttgtaggata tataattccg tattttttgg   1920

aagggtctac ttgggcttat ctatagcttt aagattccca gcacttgttt tatatattgt   1980

tttcattttt gctatgaaga aaaaatttca aggaaaagat accaaggcat cggacaatga   2040

aagaaaagta atggatgaag caaacttaga attcttaaat aatggtgaac attttgtacc   2100

ttctgctgga acagatagta aaacatgtaa tttggacatg caagacaatg ctgctgccaa   2160

ctaacattg                                                           2169
```

<210> SEQ ID NO 2
<211> LENGTH: 2712
<212> TYPE: DNA
<213> ORGANISM: Homo sapiens

<400> SEQUENCE: 2

```
gagactttaa catcagaaaa aggatggact tgttgcagtt gctgtagcat tcaaagtcaa     60

ggtgatcatt tcaaaccaag catcagcaac aattaaaaat attcacttgg tatctgtagt    120

ttaataatgg accaacatca acatttgaat aaaacagcag agtcagcatc ttcagagaaa    180

aagaaaacaa gacgctgcaa tggattcaag atgttcttgg cagccctgtc attcagctat    240

attgctaaag cactaggtgg aatcattatg aaaatttcca tcactcaaat agaaaggaga    300

tttgacatat cctcttctct tgctggttta attgatggaa gctttgaaat tggaaatttg    360

cttgtgattg tatttgtaag ttactttgga tctaaactac acagaccgaa gttaattgga    420

attggttgtc tccttatggg aactggaagt attttgacat ctttaccaca tttcttcatg    480

ggatattata ggtattctaa agaaacccat attaatccat cagaaaattc aacatcaagt    540

ttatcaacct gtttaattaa tcaaacctta tcattcaatg gaacatcacc tgagatagta    600

gaaaaagatt gtgtaaagga atctgggtca cacatgtgga tctatgtctt catggggaat    660

atgcttcgtg gcatagggga aacccccata gtaccattgg ggatttcata cattgatgat    720

tttgcaaaag aaggacattc ttccttgtat ttaggtagtt tgaatgcaat aggaatgatt    780

ggtccagtca ttggctttgc actgggatct ctgtttgcta aaatgtacgt ggatattgga    840

tatgtagatc tgagcactat cagaataact cctaaggact ctcgttgggt tggagcttgg    900
```

-continued

```
tggcttggtt tccttgtgtc tggactattt tccattattt cttccatacc attttttttc    960

ttgccgaaaa atccaaataa accacaaaaa gaaagaaaaa tttcactatc attgcatgtg   1020

ctgaaaacaa atgatgatag aaatcaaaca gctaatttga ccaaccaagg aaaaaatgtt   1080

accaaaaatg tgactggttt tttccagtct ttgaaaagca tccttaccaa tcccctgtat   1140

gttatatttc tgcttttgac attgttacaa gtaagcagct ttattggttc ttttacttac   1200

gtctttaaat atatggagca acagtacggt cagtctgcat ctcatgctaa ctttttgttg   1260

ggaatcataa ccattcctac ggttgcaact ggaatgtttt taggaggatt tatcattaaa   1320

aaattcaaat tgtctttagt tggaattgcc aaattttcat ttcttacttc gatgatatcc   1380

ttcttgtttc aacttctata tttccctcta atctgcgaaa gcaaatcagt tgccggccta   1440

accttgacct atgatggaaa taattcagtg gcatctcatg tagatgtacc actttcttat   1500

tgcaactcag agtgcaattg tgatgaaagt cagtgggaac cagtctgtgg gaacaatgga   1560

ataacttacc tgtcaccttg tctagcagga tgcaaatcct caagtggtat taaaaagcat   1620

acagtgtttt ataactgtag ttgtgtggaa gtaactggtc tccagaacag aaattactca   1680

gcacacttgg gtgaatgccc aagagataat acttgtacaa ggaaattttt catctatgtt   1740

gcaattcaag tcataaactc tttgttctct gcaacaggag gtaccacatt tatcttgttg   1800

actgtgaaga ttgttcaacc tgaattgaaa gcacttgcaa tgggtttcca gtcaatggtt   1860

ataagaacac taggaggaat tctagctcca atatattttg gggctctgat tgataaaaca   1920

tgtatgaagt ggtccaccaa cagctgtgga gcacaaggag cttgtaggat atataattcc   1980

gtattttttg gaagggtcta cttgggctta tctatagctt taagattccc agcacttgtt   2040

ttatatattg ttttcatttt tgctatgaag aaaaaatttc aaggaaaaga taccaaggca   2100

tcggacaatg aaagaaaagt aatggatgaa gcaaacttag aattcttaaa taatggtgaa   2160

cattttgtac cttctgctgg aacagatagt aaaacatgta atttggacat gcaagacaat   2220

gctgctgcca actaacattg cattgattca ttaagatgtt atttttgagg tgttcctggt   2280

ctttcactga caattccaac attctttact tacagtggac caatggataa gtctatgcat   2340

ctataataaa ctataaaaaa tgggagtacc catggttagg atatagctat gcctttatgg   2400

ttaagattag aatatatgat ccataaaaat ttaaagtgag aggcatggtt agtgtgtgat   2460

acaataaaaa gtaattgttt ggtagttgta actgctaata aaaccagtga ctagaatata   2520

agggaggtaa aaaggacaag atagattaat agcctaaata aagagaaaag cctgatgcct   2580

ttaaaaaaaa tgaaacactt tggatgtatt acttaggcca aaatctggcc tggatttatg   2640

ctataatata tattttcatg ttaagttgta tatttttcag aaattataaa tattattaat   2700

ttaaaatttg aa                                                       2712
```

<210> SEQ ID NO 3
<211> LENGTH: 702
<212> TYPE: PRT
<213> ORGANISM: Homo sapiens

<400> SEQUENCE: 3

```
Met Asp Gln His Gln His Leu Asn Lys Thr Ala Glu Ser Ala Ser Ser
1               5                   10                  15

Glu Lys Lys Lys Thr Arg Arg Cys Asn Gly Phe Lys Met Phe Leu Ala
            20                  25                  30

Ala Leu Ser Phe Ser Tyr Ile Ala Lys Ala Leu Gly Gly Ile Ile Met
        35                  40                  45
```

```
Lys Ile Ser Ile Thr Gln Ile Glu Arg Arg Phe Asp Ile Ser Ser Ser
    50                  55                  60

Leu Ala Gly Leu Ile Asp Gly Ser Phe Glu Ile Gly Asn Leu Leu Val
65                  70                  75                  80

Ile Val Phe Val Ser Tyr Phe Gly Ser Lys Leu His Arg Pro Lys Leu
                85                  90                  95

Ile Gly Ile Gly Cys Leu Leu Met Gly Thr Gly Ser Ile Leu Thr Ser
            100                 105                 110

Leu Pro His Phe Phe Met Gly Tyr Tyr Arg Tyr Ser Lys Glu Thr His
        115                 120                 125

Ile Asn Pro Ser Glu Asn Ser Thr Ser Ser Leu Ser Thr Cys Leu Ile
    130                 135                 140

Asn Gln Thr Leu Ser Phe Asn Gly Thr Ser Pro Glu Ile Val Glu Lys
145                 150                 155                 160

Asp Cys Val Lys Glu Ser Gly Ser His Met Trp Ile Tyr Val Phe Met
                165                 170                 175

Gly Asn Met Leu Arg Gly Ile Gly Glu Thr Pro Ile Val Pro Leu Gly
            180                 185                 190

Ile Ser Tyr Ile Asp Asp Phe Ala Lys Glu Gly His Ser Ser Leu Tyr
        195                 200                 205

Leu Gly Ser Leu Asn Ala Ile Gly Met Ile Gly Pro Val Ile Gly Phe
    210                 215                 220

Ala Leu Gly Ser Leu Phe Ala Lys Met Tyr Val Asp Ile Gly Tyr Val
225                 230                 235                 240

Asp Leu Ser Thr Ile Arg Ile Thr Pro Lys Asp Ser Arg Trp Val Gly
                245                 250                 255

Ala Trp Trp Leu Gly Phe Leu Val Ser Gly Leu Phe Ser Ile Ile Ser
            260                 265                 270

Ser Ile Pro Phe Phe Phe Leu Pro Lys Asn Pro Asn Lys Pro Gln Lys
        275                 280                 285

Glu Arg Lys Ile Ser Leu Ser Leu His Val Leu Lys Thr Asn Asp Asp
    290                 295                 300

Arg Asn Gln Thr Ala Asn Leu Thr Asn Gln Gly Lys Asn Val Thr Lys
305                 310                 315                 320

Asn Val Thr Gly Phe Phe Gln Ser Leu Lys Ser Ile Leu Thr Asn Pro
                325                 330                 335

Leu Tyr Val Ile Phe Leu Leu Leu Thr Leu Leu Gln Val Ser Ser Phe
            340                 345                 350

Ile Gly Ser Phe Thr Tyr Val Phe Lys Tyr Met Glu Gln Gln Tyr Gly
        355                 360                 365

Gln Ser Ala Ser His Ala Asn Phe Leu Leu Gly Ile Ile Thr Ile Pro
    370                 375                 380

Thr Val Ala Thr Gly Met Phe Leu Gly Gly Phe Ile Ile Lys Lys Phe
385                 390                 395                 400

Lys Leu Ser Leu Val Gly Ile Ala Lys Phe Ser Phe Leu Thr Ser Met
                405                 410                 415

Ile Ser Phe Leu Phe Gln Leu Leu Tyr Phe Pro Leu Ile Cys Glu Ser
            420                 425                 430

Lys Ser Val Ala Gly Leu Thr Leu Thr Tyr Asp Gly Asn Asn Ser Val
        435                 440                 445

Ala Ser His Val Asp Val Pro Leu Ser Tyr Cys Asn Ser Glu Cys Asn
    450                 455                 460

Cys Asp Glu Ser Gln Trp Glu Pro Val Cys Gly Asn Asn Gly Ile Thr
```

```
465                 470                 475                 480

Tyr Leu Ser Pro Cys Leu Ala Gly Cys Lys Ser Ser Ser Gly Ile Lys
                485                 490                 495

Lys His Thr Val Phe Tyr Asn Cys Ser Cys Val Glu Val Thr Gly Leu
            500                 505                 510

Gln Asn Arg Asn Tyr Ser Ala His Leu Gly Glu Cys Pro Arg Asp Asn
        515                 520                 525

Thr Cys Thr Arg Lys Phe Phe Ile Tyr Val Ala Ile Gln Val Ile Asn
    530                 535                 540

Ser Leu Phe Ser Ala Thr Gly Gly Thr Thr Phe Ile Leu Leu Thr Val
545                 550                 555                 560

Lys Ile Val Gln Pro Glu Leu Lys Ala Leu Ala Met Gly Phe Gln Ser
                565                 570                 575

Met Val Ile Arg Thr Leu Gly Gly Ile Leu Ala Pro Ile Tyr Phe Gly
            580                 585                 590

Ala Leu Ile Asp Lys Thr Cys Met Lys Trp Ser Thr Asn Ser Cys Gly
        595                 600                 605

Ala Gln Gly Ala Cys Arg Ile Tyr Asn Ser Val Phe Phe Gly Arg Val
    610                 615                 620

Tyr Leu Gly Leu Ser Ile Ala Leu Arg Phe Pro Ala Leu Val Leu Tyr
625                 630                 635                 640

Ile Val Phe Ile Phe Ala Met Lys Lys Lys Phe Gln Gly Lys Asp Thr
                645                 650                 655

Lys Ala Ser Asp Asn Glu Arg Lys Val Met Asp Glu Ala Asn Leu Glu
            660                 665                 670

Phe Leu Asn Asn Gly Glu His Phe Val Pro Ser Ala Gly Thr Asp Ser
        675                 680                 685

Lys Thr Cys Asn Leu Asp Met Gln Asp Asn Ala Ala Ala Asn
    690                 695                 700


<210> SEQ ID NO 4
<211> LENGTH: 33
<212> TYPE: DNA
<213> ORGANISM: Homo sapiens

<400> SEQUENCE: 4

atgggatggc ttggcttggg ctcagagacc tga                                33


<210> SEQ ID NO 5
<211> LENGTH: 10
<212> TYPE: PRT
<213> ORGANISM: Homo sapiens

<400> SEQUENCE: 5

Met Gly Trp Leu Gly Leu Gly Ser Glu Thr
1               5                   10


<210> SEQ ID NO 6
<211> LENGTH: 84
<212> TYPE: DNA
<213> ORGANISM: Homo sapiens

<400> SEQUENCE: 6

atggccacgt tactgaatct acatgttgca agagaaaaac tagcagatgt tcttggcagc     60

cctgtcattc agctatattg ctaa                                            84


<210> SEQ ID NO 7
```

```
<211> LENGTH: 27
<212> TYPE: PRT
<213> ORGANISM: Homo sapiens

<400> SEQUENCE: 7

Met Ala Thr Leu Leu Asn Leu His Val Ala Arg Glu Lys Leu Ala Asp
1               5                   10                  15

Val Leu Gly Ser Pro Val Ile Gln Leu Tyr Cys
            20                  25


<210> SEQ ID NO 8
<211> LENGTH: 63
<212> TYPE: DNA
<213> ORGANISM: Homo sapiens

<400> SEQUENCE: 8

atgaaaattt ccatcactca aatagaaagg agatttgaca tatcctcttc tcttgctggt     60

tga                                                                   63


<210> SEQ ID NO 9
<211> LENGTH: 20
<212> TYPE: PRT
<213> ORGANISM: Homo sapiens

<400> SEQUENCE: 9

Met Lys Ile Ser Ile Thr Gln Ile Glu Arg Arg Phe Asp Ile Ser Ser
1               5                   10                  15

Ser Leu Ala Gly
            20


<210> SEQ ID NO 10
<211> LENGTH: 132
<212> TYPE: DNA
<213> ORGANISM: Homo sapiens

<400> SEQUENCE: 10

atggcttggc ttgggctcag agacctgaca gtggcaatgt atggccacgt tactgaatct     60

acatgttgca agagaaaaac tagcagatgt tcttggcagc cctgtcattc agctatattg    120

ctaaagcact ag                                                        132


<210> SEQ ID NO 11
<211> LENGTH: 43
<212> TYPE: PRT
<213> ORGANISM: Homo sapiens

<400> SEQUENCE: 11

Met Ala Trp Leu Gly Leu Arg Asp Leu Thr Val Ala Met Tyr Gly His
1               5                   10                  15

Val Thr Glu Ser Thr Cys Cys Lys Arg Lys Thr Ser Arg Cys Ser Trp
            20                  25                  30

Gln Pro Cys His Ser Ala Ile Leu Leu Lys His
        35                  40


<210> SEQ ID NO 12
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 12
```

tgcaccacca actgctta 18

<210> SEQ ID NO 13
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 13
ggatgcaggg atgatgttc 19

<210> SEQ ID NO 14
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 14
gccacgaagc atattcccca tgaag 25

<210> SEQ ID NO 15
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 15
ttccagttcc cataaggaga caacc 25

<210> SEQ ID NO 16
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 16
gtgcaagtca caggggatgg ga 22

<210> SEQ ID NO 17
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 17
gctgaatgac agggctgcca ag 22

<210> SEQ ID NO 18
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 18
gcaatgttag ttggcagcag ca 22

<210> SEQ ID NO 19
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 19
ggtatctgta gtttaataat ggacc 25

<210> SEQ ID NO 20
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 20
gaaagaccag gaacacctca 20

<210> SEQ ID NO 21
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 21
ttggcttggg ctcagaga 18

<210> SEQ ID NO 22
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 22
tgccaagaac atctgctagt tt 22

<210> SEQ ID NO 23
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 23
aacagcagag tcagcatctt cag 23

<210> SEQ ID NO 24
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 24
aacatcttga atccattgca gc 22

<210> SEQ ID NO 25
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 25
cctctagagg gatgggatgg cttggcttgg gctcagagac cgtgagcaag ggcg 54

<210> SEQ ID NO 26
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 26
ggggtacctt acttgtacag ctcatccatg ccg 33

<210> SEQ ID NO 27
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 27
gctctagagt gcaagtcaca ggggatggga 30

<210> SEQ ID NO 28
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 28
gtggatccgc aatatagctg aatgacaggg 30

<210> SEQ ID NO 29
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 29
taggatccac cagcaagaga agagga 26

<210> SEQ ID NO 30
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 30
tcggatccgt gctttagcaa tatagctgaa t 31

<210> SEQ ID NO 31
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 31
cgggatccgt gagcaagggc gccgagc 27

<210> SEQ ID NO 32

-continued

```
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 32

ggggtacctt acttgtacag ctcatccatg ccg                              33
```

ALTERNATIVE SPLICING VARIANT OF OATP1B3 MRNA

CROSS-REFERENCE TO RELATED APPLICATIONS

This application is a divisional of application Ser. No. 13/030,485 filed on Feb. 18, 2011, which claims the benefit under 35 U.S.C. § 119 of Japanese Applications No. 2010-035166 and No. 2011-032501, filed on Feb. 19, 2010, and Feb. 17, 2011, respectively. This application is related to application Ser. No. 13/759,101 filed Feb. 5, 2013, now U.S. Pat. No. 9,115,405, which is also a divisional of application Ser. No. 13/030,485. The contents of all four previously filed applications are incorporated herein by reference in their entirety.

BACKGROUND

Technical Field

The present invention relates to a novel tumor marker. In more detail, the present invention relates to a novel alternative splicing variant of OATP1B3 mRNA, and use thereof.

Background Art

Along with recent advances in medical technology, technology for cancer therapy has also been improved extensively, and it can occasionally be seen that there are some types of cancers which show declining trend of mortality rates. However, findings of cancer development in early stage influence on the therapeutic effects, and establishment of a method which enables to detect the tumor at early stage has been desired.

As to the diagnosis of cancer, in addition to the methods which detect cancer tissues visually by ultrasound or X-ray, the method for detecting abnormality such as cell morphology in the tissue collected from a patient by immunohistological procedures, as well as biochemical, immunochemical detection methods for the dynamic state of so called tumor marker such as specific protein or gene which may cause alteration in their expression in association with the development of a specific cancer, have been known.

In these methods, the method in which the tissue is observed for its morphology by an immunohistological procedure needs for preparing tissue specimen, and takes time to ascertain the presence of cancer development, and moreover, the method will require much skill to identify the presence of cancer development from the morphology observed.

Therefore, application of the method which employs the tumor markers which can judge the presence or absence of cancer development relatively simply and objectively, has been often performed. However, since many of the tumor markers employed in the human cancer diagnosis are also expressed to some extent in the normal tissue cell, and variation of expression of the aforementioned tumor marker has to be employed as an index of malignant alteration in many cases, there always remains possibility of a wrong diagnosis.

Therefore, for the purpose of detecting presence of cancer development objectively and more correctly, it is desirable to use a substance as a tumor marker which is not detectable in non-cancer cell, but is produced only by cancerous cell. Taking a pancreatic cancer as an example, because there is no effective screening test method for pancreatic cancer at the present time, it may be too late for treatment at the time when the symptom of cancer has appeared in many cases, it would be necessary to use a specific tumor marker for pancreatic cancer to detect the pancreatic cancer in early stage.

By the way, organic anion transporting polypeptide 1B3 (OATP1B3, genetic name: SLCO1B3) is a transporter expressed on the cell membrane showing broad substrate recognition property, and is involved in uptake of various compounds comprising anti-cancer drugs into a cell. The OATP 1B3 is normally expressed specifically in hepatic cells; however, the expression will also be found in other organs in association with the tissue becoming cancerous. Up to now, it has been reported that the expression and the function of OATP1B3 affect patient's survival rate in breast cancer and prostate cancer (see, Non-patent Literatures 1 and 2). In addition, in the analysis using colorectal cancer cells, it has been reported that the expression of OATP1B3 gives the cell having resistance against apoptosis (see, Non-patent Literature 3).

From the things described above, it is conceivable that the OATP1B3 may be involved in a certain role in the cancer cell. For this reason, detection of the OATP1B3 is useful for prognostic diagnosis and efficacy evaluation of anti-cancer drug in cancer therapy, and expected to be a useful tumor marker. For example, Patent Literature 1 discloses a technology to measure expression of LST-2 in cancer tissue from female colorectal cancer patients using anti-LST-2 monoclonal antibody which recognizes C-terminal intracellular domain of LST-2 (another name of OATP1B3), and predict prognosis of the patient based on the measurement value.

However, there are many points remaining still unknown with respect to expression and function of OATP1B3 in cancer cells, and it is present situation that a method of using of OATP1B3 as a tumor marker is not well-established.

PRIOR ART LITERATURES

Patent Literatures

Patent Literature 1: JP-A-2007-119390

Non-Patent Literatures

Non-patent Literature 1: Muto et al. Human liver-specific organic anion transporter-2 is a potent prognostic factor for human breast carcinoma. (2007) Cancer Sci. 98:1570-6;

Non-patent Literature 2: Hamada et al. Effect of SLCO1B3 Haplotype on Testosterone Transport and Clinical Outcome in Caucasian Patients with Androgen-Independent Prostatic Cancer (2008) Clin. Cancer Res. 14:3312-8;

Non-patent Literature 3: Lee et al. Overexpression of OATP1B3 confers apoptotic resistance in colon cancer. (2008) Cancer Res. 68:10315-23.

SUMMARY OF INVENTION

Problem to be Solved by the Invention

In view of the conventional technology as described above, an object of the present invention is to provide a novel tumor marker and use thereof. In more detail, the present invention is directed to provide a novel tumor marker, a measurement method and a measurement kit for the aforementioned tumor marker, a method for detecting cancer using the same, a kit for detecting cancer, a method for screening a preventive and/or therapeutic agent for cancer, as well as a medicament such as cancer vaccine.

Means for Solving the Problem

With the view to the conventional technology mentioned above, the inventors of the present invention have studied intensively for the purpose of further investigation on expression and function of OATP1B3. On the way of the investigation, the inventors have obtained surprisingly the following 3 findings:

(1) there exists an alternative splicing variant of the conventionally reported OATP1B3 mRNA (herein, also referred to as "OATP1B3/wt"; "wt" means wild type);

(2) this novel alternative splicing variant is expressed specifically and strongly in cancer cell and tissue; and (3) from this new alternative splicing variant, some peptides or proteins can be expressed; (herein, this alternative splicing variant is also referred to as "OATP1B3/ct", "ct" means cancer type), and accomplished the present invention based on these findings.

That is, according to the 1st aspect of the present invention, there is provided a method for measuring an alternative splicing variant of OATP1B3 mRNA in a sample to be examined. The aforementioned measurement method comprises measuring a mRNA comprising a nucleotide sequence represented by SEQ ID NO: 1 in the sequence listing table in the aforementioned sample to be examined with differentiation from a mRNA comprising a nucleotide sequence represented by SEQ ID NO: 2.

On this occasion, it is preferable that the OATP1B3/ct is measured using the presence of exon SV in the nucleotide sequence represented by SEQ ID NO: 1 as an indicator (details about "exon SV" will be mentioned later). In addition, this measurement comprises specifically amplifying the OATP1B3/ct or a partial region of cDNA thereof, for example, by a nucleic acid amplification method using a primer set in the region containing exon SV as one primer, and measuring the amplification product. In addition, the number of nucleotide of the aforementioned primer is preferably about 15 to about 35. Moreover, the aforementioned nucleic acid amplification method is preferably RT-PCR method.

In addition, according to the 2nd aspect of the present invention, there is provided a nucleic acid satisfying the following conditions:

(1) a nucleic acid which is capable of hybridizing with the nucleic acid comprising a nucleotide sequence represented by SEQ ID NO: 1 under a stringent condition;

(2) a nucleic acid which, when a nucleic acid comprising a nucleotide sequence represented by SEQ ID NO: 2 is coexisting, does not hybridize with such nucleic acid under a stringent condition, or else even if hybridized with such nucleic acid, 3' terminal thereof serves as a mismatch.

On this occasion, the aforementioned nucleic acid preferably hybridizes with a region comprising exon SV. In addition, the number of nucleotide of the aforementioned nucleic acid is preferably about 10 or more, more preferably about 15 to about 35. Furthermore, the aforementioned nucleic acid preferably consists of a nucleotide sequence represented by SEQ ID NO: 1 or the same nucleotide sequence as a partial region of the aforementioned nucleotide sequence, or the nucleotide sequence in which 10% or less of nucleotides of these nucleotide sequences have been replaced. Such nucleic acid is suitably employed for the measurement of an alternative splicing variant of OATP1B3 mRNA. On this occasion, the aforementioned nucleic acid is preferably a primer or a probe for nucleic acid amplification.

Furthermore, according to the 3rd aspect of the present invention, there is provided a measurement kit for an alternative splicing variant of OATP1B3 mRNA comprising the nucleic acids provided by the 2nd aspect of the present invention.

In addition, according to the 4th aspect of the present invention, there is also provided a detection method of cancer. The aforementioned detection method comprises measuring an alternative splicing variant of OATP1B3 mRNA in a sample to be examined isolated from living organism by the measurement method provided by the 1st aspect of the present invention, or by using the measurement kit provided by the 3rd aspect of the present invention. On this occasion, it is preferable to measure an alternative splicing variant of OATP1B3 mRNA comprising the nucleotide sequence represented by SEQ ID NO: 1. Moreover, in the aforementioned detection method, the cancer is preferably colorectal cancer or pancreatic cancer.

Furthermore, according to the 5th aspect of the present invention, there is also provided a method for screening a preventive and/or therapeutic agent for cancer. The aforementioned screening method comprises a step where an alternative splicing variant of OATP1B3 mRNA in a cultured cell obtained by culturing cancer cell in the presence of test substance is measured by the measurement method provided by the 1st aspect of the present invention, or by using the measurement kit provided by the 3rd aspect of the present invention; and a step where the obtained measurement result is compared with the result in the case where the aforementioned test substance is absent and/or evaluated.

And, according to the 6th aspect of the present invention, there is also provided an alternative splicing variant of OATP1B3 mRNA comprising the nucleotide sequence represented by SEQ ID NO: 1 itself. The alternative splicing variant can be used, for example, for the screening method of the 5th aspect of the present invention by introducing the aforementioned variant into cells in culture, being forced expression thereof, and producing cancellation-acquired cells in culture and the like.

In addition, according to the 7th aspect of the present invention, there is provided the following polypeptide:

(1) a polypeptide which comprises an amino acid sequence represented by SEQ ID NO: 5, SEQ ID NO: 7, SEQ ID NO: 9, or SEQ ID NO: 11, and enhances expression thereof in cancer cell or cancer tissue; or (2) a polypeptide which comprises an amino acid sequence in which 10% or less of amino acids are replaced, deleted, and/or inserted in the amino acid sequence represented by SEQ ID NO: 5, SEQ ID NO: 7, SEQ ID NO: 9, or SEQ ID NO: 11, and enhances expression thereof in cancer cell or cancer tissue. The aforementioned polypeptide is preferably a polypeptide consisting of the amino acid represented by SEQ ID NO: 5, SEQ ID NO: 7, SEQ ID NO: 9, or SEQ ID NO: 11.

Furthermore, according to the 8th aspect of the present invention, there are also provided a nucleic acid encoding the polypeptide of the 7th aspect, an expression vector comprising the aforementioned nucleic acid, and a cell transformed by the aforementioned expression vector.

In addition, according to the 9th aspect of the present invention, there are also provided an antibody which is capable of binding to the polypeptide of the 7th aspect, and a nucleic acid hybridizing with the nucleic acid comprising a nucleotide sequence represented by SEQ ID NO: 4, SEQ ID NO: 6, SEQ ID NO: 8, or SEQ ID NO: 10 under stringent condition, having at least 15 nucleotides.

And, according to the 10th aspect of the present invention, there is provided a detection method for cancer comprising measuring the amount of polypeptide of the aforementioned 7th aspect in a sample to be examined isolated from living organism. On this occasion, it is preferable to employ the antibody of the aforementioned 9th aspect for the measurement. Also, a detection kit for cancer comprising the aforementioned antibody can be provided.

In the 11th aspect of the present invention, a medicament is provided. The aforementioned medicament comprises the polypeptide of the 7th aspect or a fragment thereof, or the nucleic acid of the 8th aspect or a fragment thereof, and is the one to be used for inducing a specific cytotoxic T cell. The aforementioned medicament is preferably a cancer vaccine.

Effect of the Invention

According to the present invention, a novel alternative splicing variant of human OATP1B3 mRNA is provided as a new cancer marker, and also a measurement method for the same, a nucleic acid which can be used for the aforementioned measurement, and a means for practicing the aforementioned measurement method (a kit for measurement) are provided. In addition, according to the present invention, a new method for detecting cancer is also provided, and further, a new method for screening a preventive and/or therapeutic agent for cancer is also provided. In addition, there are also provided a polypeptide which can be used for detecting cancer and an antibody binding thereto, a method for detecting cancer using the amount of the aforementioned polypeptide as an indicator, a kit for detecting cancer comprising the aforementioned antibody, and a medicament as a cancer vaccine and the like.

BRIEF DESCRIPTION OF THE DRAWINGS

FIG. 1A, FIG. 1B, and FIG. 1C, combined ("FIG. 1"), show the results of alignment carried out for the nucleotide sequence of cDNA of OATP1B3/ct (SEQ ID NO: 1) and the nucleotide sequence of cDNA of OATP1B3/wt (SEQ ID NO: 2). In FIG. 1, an asterisk (*) means that the nucleotide is identical between the two nucleotide sequences.

In FIG. 4, the locations of known and new transcription start sites are shown. In addition, the positions where the primer set used in the RT-PCR performed in Example hybridize are also indicated by arrow, respectively.

FIG. 6-A shows the expression level of OATP1B3/ct in each tissue and cell. In addition, FIG. 6-B shows the expression level of OATP1B3/wt in each tissue and cell. Further, FIG. 6-C shows the ratios of expression level (copy number of OATP1B3/ct versus copy number of OATP1B3/wt).

FIG. 7 is a figure showing four open reading frames (ORF) locating on OATP1B3/ct. The nucleotide sequence of cDNA is shown in the upper sequence, and the amino acid sequence coded thereby is shown in the lower sequence. In addition, the underline indicates ORF, and bold-faced ATG indicates the estimated translation initiation codon locating on the upstream of ORF. The sign "GFP" as shown in the amino acid sequence to be encoded indicates the site where the nucleotide sequence encoding green fluorescent protein (GFP) was inserted when the expression plasmid was constructed in Example. It should be noted that, as for frame 2, the expression vector was constructed by inserting the nucleotide sequence encoding GFP into a position behind the region encoding N-terminal 20 amino acids.

DETAILED DESCRIPTION

Figures 2, 3:
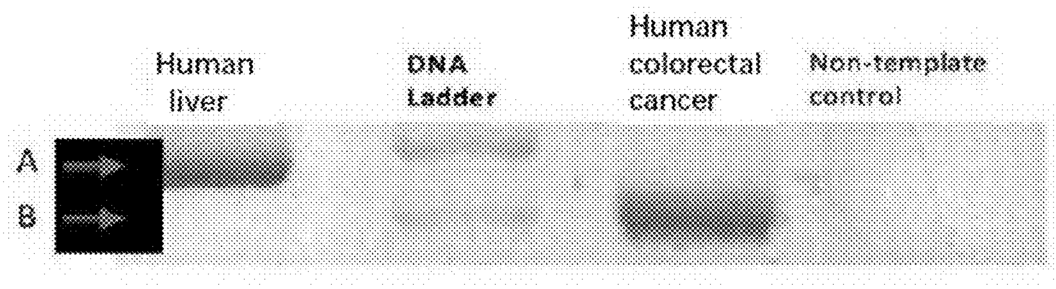
FIG. 2 is a figure showing the amino acid sequence of the protein encoded by OATP1B3/wt.
FIG. 3 is a photograph showing the results of agarose gel electrophoresis performed to visualize the results of RLM-5'-RACE method carried out using the total RNA derived from human colon cancer or the total RNA derived from the Caucasian liver as a template in "5. Determination of transcription starting point of SLCO1B3 gene" in Example.

Human SLCO1B3 is a gene of about 106 kbp locating on a chromosome 12p12, and from this gene, OATP1B3 mRNA (OATP1B3/wt; Refseq Accession No. NM_019844) which consists of 2712 bp (15 exons) is transcribed. The nucleotide sequence of cDNA of this OATP1B3/wt which has already been reported is represented by SEQ ID NO: 2 and FIG. 1. This OATP1B3/wt encodes a protein which consists of 702 amino acids (OATP1B3 protein; RefSeq Accession No. NP_062818). The amino acid sequence of the protein which is encoded by this OATP1B3/wt is represented by SEQ ID NO: 3 and FIG. 2. In addition, in the nucleotide sequence represented by SEQ ID NO: 2, the 1st nucleotide from 5' terminal (herein, referred to as "1 nt"; the nucleotides at other positions are called similarly by adding nt to the number of position where the nucleotide is located from 5' terminal) to 61 nt is exon 1; 62 nt to 210 nt is exon 2; 211 nt to 1991 nt is exon 3 to exon 14; and 1992 nt to 2712 nt is exon 15. In addition, the coding sequence (CDS; Coding Sequence) of OATP1B3/wt is 127 to 2235 nt (the stop codon TAA is included) over exon 2 to exon 15, and is written by capital letters in FIG. 1. On the other hand, the non-coding region of OATP1B3/wt is written by lower-case letters in FIG. 1.

As described in Example mentioned later, the inventors of the present invention found that when the RLM-5'-RACE method was carried out for the purpose of determining the transcription starting site of human SLCO1B3 gene using the total RNA derived from human colon cancer tissue as a template, the amplification product with smaller molecular weight than the size expected from the reported information on the transcription starting site ("TSS" shown in FIG. 1) was detected. And, when the nucleotide sequence nearby the novel transcription starting site of the SLCO1B3 gene was compared with the database of human genomic DNA, it was clarified that the novel transcription starting site was located in the region of the intron 2 in SLCO1B3 gene, and furthermore, new exon existed in this region also (this new exons is referred to as "exon SV"). Moreover, this exon SV had been spliced to exon 3 in OATP1B3/wt (see, FIG. 4 mentioned later). The nucleotide sequence of cDNA of a novel alternative splicing variant (OATP1B3/ct) of thus discovered OATP1B3 mRNA is represented by SEQ ID NO: 1 and FIG. 1.

As mentioned above, exon SV of OATP1B3/ct has been spliced to exon 3 of OATP1B3/wt. That is, in the nucleotide sequence represented by SEQ ID NO: 1, the sequence from 1 nt to 139 nt is the exon SV. In addition, the sequence from 140 nt to 1920 nt in the nucleotide sequence represented by SEQ ID NO: 1 has substantially the same sequence to the sequence from exon 3 to exon 14 of OATP1B3/wt. And, the nucleotide sequence from 1921 nt to 2170 nt in the nucleotide sequence represented by SEQ ID NO: 1 has the same sequence to the corresponding region of exon 15 of OATP1B3/wt.

It was confirmed that an expression level of the alternative splicing variant found in the present invention (for example, OATP1B3/ct) was increased in cancer cell, as described later in Example. Therefore, it is possible to detect cancer by measuring the aforementioned alternative splicing variant in a sample to be examined isolated from the living organism.

Hereinafter, the specific preferable embodiments of the present invention will be described in detail, however, the technical scope of the present invention should be defined based on the descriptions of claims, and should not be limited by the following illustrative embodiments and Examples.

The measurement method for alternative splicing variant of OATP1B3 mRNA provided in the 1st aspect of the present invention comprises measuring a mRNA comprising a nucleotide sequence represented by SEQ ID NO: 1 (for example, the mRNA consisting of the nucleotide sequence represented by SEQ ID NO: 1) in the aforementioned sample to be examined with differentiation from a mRNA comprising a nucleotide sequence represented by SEQ ID NO: 2 (for example, the mRNA consisting of the nucleotide sequence represented by SEQ ID NO: 2). It should be noted that, since the nucleotide sequence represented by SEQ ID NO:1 indicates both of nucleotide sequences of mRNA and cDNA obtained using the same as a template, when mRNA is referred to, of course, since uracil (u) may be contained in place of thymine (t), "t" can be replaced by "u". In addition, "measurement" encompasses any concept of quantitative measurement, semi-quantitative measurement and detection. Furthermore, "measurement of mRNA" encompasses, in addition to a case of measuring mRNA directly, a case where after the mRNA is once converted to cDNA, the aforementioned cDNA is measured (RT-PCR and the like as described later), and a case where the mRNA is measured indirectly such as the case when translation product of the mRNA is measured. Moreover, in the following description, mRNA, cDNA, nucleic acid and so on which comprises the nucleotide sequence represented by SEQ ID NO: 1 are sometimes referred to as "mRNA of SEQ ID NO: 1, cDNA of SEQ ID NO: 1, nucleic acid of SEQ ID NO: 1, and so on", respectively.

In addition, in the sequence listing, even if it is double stranded nucleic acid, only a single strand of them (a sense strand for the nucleic acid encoding a polypeptide) is to be indicated according to the rule. For this reason, in the case of double stranded nucleic acid, even if the sequence indicated actually in the sequence listing is a single strand, it can be understood that actually a strand complementary to the indicated strand is also indicated in the sequence listing. Therefore, in the present application, when the nucleic acid which comprises or consists of the nucleotide sequence shown in a certain SEQ ID NO is or may be double stranded nucleic acid, the nucleotide sequence shown in the SEQ ID NO shall also include the complementary strand thereof, except for the case where it is clearly not right from the context. For example, the nucleic acid which is capable of hybridizing with the nucleic acid comprising a nucleotide sequence represented by SEQ ID NO: 1" means, in addition to a nucleic acid which is capable of hybridizing with a sense strand actually represented by SEQ ID NO: 1, a nucleic acid which is capable of hybridizing with the antisense strand consisting of the nucleotide sequence complementary to the aforementioned sense strand.

It is easy for the person skilled in the art to measure the mRNA of SEQ ID NO: 1 with identification from the mRNA of SEQ ID NO: 2, and is possible by various methods. For example, by setting primers within exon SV and in the region after exon 3 to perform reverse transcriptase-PCR (RT-PCR), and differentiating whether the mRNA is OATP1B3/wt or an alternative splicing variant (for example, OATP1B3/ct) based on the molecular weight of the amplification product, the mRNA can be measured. Moreover, as to the obtained amplification product, nucleotide sequence may be determined (direct sequencing).

As mentioned above, in the mRNA of SEQ ID NO: 1, there exist exon SV which is an exon not existing in OATP1B3/wt. Therefore, alternative splicing variant can be measured by using the presence of this exon SV as an indicator. That is, using the presence of exon SV in the nucleotide sequence represented by SEQ ID NO: 1 as an indicator, an alternative splicing variant comprising the nucleotide sequence represented by SEQ ID NO: 1 can be measured.

Preferred method for measuring an alternative splicing variant by using the presence of exon SV as an indicator includes, a method which employs nucleic acid amplification method using a primer which is capable of hybridizing with the region comprising exon SV, and a method using a probe which is capable of hybridizing with the region comprising exon SV.

The method employing nucleic acid amplification method comprises specifically amplifying mRNA comprising a nucleotide sequence represented by SEQ ID NO: 1 or a partial region of cDNA thereof by a nucleic acid amplification method using a primer set in the region containing the aforementioned exon SV as one primer, and measuring the amplification product. In this case, since "set in the region" means hybridizing with the region, and the nucleic acid to be amplified by the nucleic acid amplification method like PCR is double strand, as mentioned above, both of the case where the primer which hybridizes with the sense strand described actually on the list (reverse primer) is employed and the case where the primer which hybridizes with the antisense strand complementary to the aforementioned sense strand (forward primer) is employed are also included. Accordingly, for example, "primer set in the region comprising exon SV" means the primer which hybridizes with the region comprising exon SV (that is, 1 nt to 139 nt) of the sense strand actually described in SEQ ID NO: 1 (reverse primer), or the primer having the nucleotide sequence complementary to the aforementioned primer (forward primer). In addition, "specifically amplifying" means that although the mRNA comprising the nucleotide sequence represented by SEQ ID NO: 1 or a partial region of cDNA thereof is amplified, the mRNA comprising the nucleotide sequence represented by SEQ ID NO: 2 or a partial region of cDNA thereof is not amplified. It should be noticed that, in the nucleotide sequence represented by SEQ ID NO: 1, 1 nt to 139 nt is exon SV, and exon 3 starts from 140 nt. Therefore, in the nucleotide sequence represented by SEQ ID NO: 1, the fusion point between 139 nt and 140 nt is a specific fusion point of exon SV and exon 3 which does not exist in OATP1B3/wt. In this regard, however, as is clear from FIG. 1, two nucleotides of the upper stream side from the aforementioned specific fusion point are common to OATP1B3/wt and OATP1B3/ct. Therefore, in the nucleotide sequence represented by SEQ ID NO: 1, the fusion point between 137 nt and 138 nt which is the nearest other specific fusion point is more suitable as a specific fusion point between exon SV and exon 3 than the fusion point between 139 nt and 140 nt. For this reason, as "a region comprising exon SV" in the present description, 1 nt to 137 nt is more preferable region.

The preferable example of nucleic acid amplification method for amplifying DNA having the same nucleotide sequence (note, however, that u is replaced by t) as a partial region of mRNA to be used as a template includes the reverse transcriptase-PCR (RT-PCR). In the RT-PCR, mRNA is extracted from cell by the conventional procedure; using the mRNA as a template and by an action of reverse transcriptase, single strand cDNA is generated; further using this single strand cDNA as a template complementary strand is generated, thus the double stranded cDNA is obtained. Subsequently, PCR is carried out using the obtained double stranded cDNA as a template, the aforementioned cDNA or partial region thereof is amplified. Since RT-PCR itself is well-known technology, and a kit and equipment thereof are also commercially available, it can be carried out easily. To amplify the cDNA derived from alternative splicing variant specifically, the primer set in the region comprising the specific fusion point mentioned above is employed as one primer. The other primer can be set in the arbitrary region of splicing variant to be amplified. In addition, the primer size is not particularly limited, but usually about 15 to 35 nucleotides, and preferably about 15 to 25 nucleotides.

For example, in the case where the mRNA of SEQ ID NO: 1 is measured by the RT-PCR, the primer which has been set in the region comprising exon SV in the nucleotide sequence represented by SEQ ID NO: 1 is employed as one primer (it may be either forward primer or reverse primer). In this case, in order to amplify cDNA derived from alternative splicing variant specifically, it is preferable to use the one as a primer which hybridizes with the cDNA of SEQ ID NO: 1 under a stringent condition, but does not hybridize with the cDNA of SEQ ID NO: 2. Here, "a stringent condition" is referred to a condition under which a primer specifically hybridizes with cDNA, and for example, it may be measured according to the condition described in a text book (Sambrook, et al. ed., "Molecular Cloning, A Laboratory Manual, 2nd ed.", 1989, Coldspring Harbor Laboratory, especially in section 11. 45 "Conditions for Hybridization of Oligonucleotide Probes", etc.), and is not particularly limited. The stringent condition depends on salt concentration, temperature, and other conditions; and, for example, as salt concentration becomes lower, and temperature becomes higher, stringency becomes higher, and hybridization of primer with cDNA becomes difficult. Generally, the salt concentration is adjusted by adjusting the concentration of SSC solution (NaCl+trisodium citrate), and the stringent salt concentration is, for example, about 250 mM or less of NaCl and about 25 mM or less of trisodium citrate. The stringent temperature is generally a temperature lower by 15 to 25° C. than the melting temperature (Tm) of perfect hybridization, and, for example, about 30° C. or higher. The temperature can be lowered by adding organic solvent (for example, formamide) to the solution. Other conditions include hybridization time, concentration of detergent (for example, SDS), and presence or absence of carrier DNA, etc.; and various stringencies can be set up by combining these conditions. As a preferred example, hybridization is carried out under the conditions of 250 mM NaCl, 25 mM trisodium citrate, 1% SDS, 50% formamide, and 200 μg/mL of denatured salmon sperm DNA, at a temperature of 42° C. In addition, washing condition after hybridization also influences on the stringency. This washing condition is also defined by salt concentration and temperature, and stringency of washing increases by decreasing salt concentration and increasing temperature. As a preferred example, washing is carried out under the condition of 15 mM NaCl, 1.5 mM trisodium citrate, and 0.1% SDS, at 68° C.

In order to ensure that the hybridization occurs with the cDNA of SEQ ID NO: 1, but does not occur with the cDNA of SEQ ID NO: 2, the primer is preferably the one in which 20% or more thereof hybridize with the region comprising exon SV. Alternatively, even in the case where the hybridization occurs with cDNA of SEQ ID NO: 2, it is preferable to use such a primer in which the 3' terminal thereof serves as a mismatch. Even if hybridization occurred with cDNA of SEQ ID NO: 2 under a stringent condition, if the 3' terminal of the primer serves as a mismatch, amplification does not take place substantially. Furthermore, it is particularly preferable to employ a primer in which at least 20% or more is capable of hybridizing with the region within exon SV under the stringent condition, and the 3' terminal thereof serves as a mismatch to cDNA of SEQ ID NO: 2. By employing the above primer as one primer, even if the cDNA of SEQ ID NO: 2 is coexisting, only the cDNA of SEQ ID NO: 1 can be amplified specifically. In addition, although a primer which is completely complementary to the region in the nucleotide sequence of SEQ ID NO: 1 to be hybridized with the primer is preferable, usually, even if about 10% or less of mismatch exists, the primer can be used as a primer in many cases (however, as mentioned above, the one comprising such a mismatch in the 3' terminal of a primer should be excluded).

The PCR in itself can be performed according to the conventional procedures. And, the amplification product is measured after amplification by the PCR. Measurement of such amplification product can also be performed by the conventional procedures. As mentioned above, the "measurement" in the present invention encompasses both detection and quantitative measurement. Furthermore, simple determination or semi-quantitative measurement such as measurement of fluorescence intensity of electrophoresis band of amplification products, and visual judgment of thickness is also included in the concept of "measurement". The measurement of amplification products can be performed, for example, by subjecting the amplification products to electrophoresis, and detecting the amplified bands. In addition, the amplification product can be also measured by fluorescently labeling the amplification product by performing the PCR under the presence of fluorescently labeled nucleotide triphosphate, and measuring fluorescence intensity of the amplified band. Further, the measurement of the amplification product can be also performed by transcribing the electrophoretic pattern to the membrane consisting of nylon or nitrocellulose to hybridize a labeled probe which is capable of hybridizing with the amplification product, and detecting or determining (PCR-Southern method) the label. Furthermore, the measurement of the amplification product can be also performed by solid-phasing the probe which is capable of hybridizing with amplification products, carrying out the above-described amplification process in the presence of labeled nucleotide triphosphate to bind the amplification product to the solid-phased probe, and measuring the amplification product bound to the solid phase. All of these methods are conventional procedures, and well known knowledge may be appropriately referred to.

Alternatively, preferably the PCR of the above-described RT-PCR is carried out by real-time detection PCR, because more precise quantitative measurement of the amplification product can be performed. In the real-time detection PCR, normal PCR is carried out in the presence of a probe bound with two kinds of fluorescent dye, which is capable of hybridizing with the amplification product. One of the two kinds of fluorescent dyes is a quencher dye which negates fluorescent emission from another fluorescent dye, and fluorescence is not measured in the state where two kinds of fluorescent dyes are bound to the same probe molecule. On the other hand, if amplification is taken place by PCR, at first, the probe will hybridize with the amplification product. And, when the probe is digested by exonuclease activity of the DNA polymerase used for the amplification reaction, the two kinds of fluorescent dyes become apart, and extinction by quencher dye does not occur, and as a consequent, fluorescence becomes measurable. Since number of cycles at which the fluorescence intensity measured increase rapidly may vary depending on the concentration of template nucleic acid in a sample, the concentration of template nucleic acid in the sample can be measured quantitatively by measuring fluorescence of reaction solution continuously. In addition, the real-time detection PCR in itself is well-known technology, and since the kit for it is also commercially available, it can be easily carried out employing the kit in the market.

It should be noted that, when the RT-PCR is performed, amplification may take place sometimes using pseudogene as a template which is contained in the genomic DNA contaminated when mRNA is first extracted. Therefore, as for the primer set to be used, it is preferable that the set is the one in which the primers have been selected so as not to cause the amplification resulting from such a pseudogene. Whether the amplification resulting from a pseudogene take place or not can be determined, for example, by whether only the amplification product of the same size as the case where PCR is performed by employing cDNA as a template is formed or not, when PCR is performed using the primer set concerned, and using the genomic DNA as a template. The primer sets (Table 3) exactly employed in the Example mentioned later are the ones which do not cause such amplification resulting from a pseudogene. Also, in some cases, before performing RT-PCR, PCR is carried out using the RNA to be used as a template, and using a primer set which amplifies housekeeping genes, such as human glyceraldehyde-3-phosphate dehydrogenase (GAPDH) (for example, the one which is listed in Table 1), and by checking that an amplification products is not acquired, it can be guaranteed that there is no contamination of genomic DNA.

As mentioned above, although the measurement method of the present invention was explained in detail by taking the case where measurement was performed by the RT-PCR method as an example, the measurement method of the present invention is not limited to the RT-PCR method, and any other method utilizing the nucleic acid amplification method may be used, so long as it is the one in which mRNA of alternative splicing variant or cDNA or partial region thereof is amplified using the aforementioned primer. For example, mRNA can also be amplified by the NASBA method (3SR method, TMA method). In the NASBA method, the reverse primer in which T7 promoter sequence is attached to 5' terminal thereof is used as a reverse primer in the presence of reverse transcriptase such as AMT-RT and the like, to form cDNA strand (antisense strand) using mRNA as a template. RNA strand of the obtained RNA/DNA hybrid double strand is digested by RNase H to generate a single-stranded cDNA (antisense strand). Subsequently, using this single-stranded cDNA as a template, a complementary strand is formed using forward primer in the presence of DNA polymerase (when AMT-RT is used as a reverse transcriptase, the AMT-RT can serve as DNA polymerase because it possesses DNA polymerase activity), and thus double-stranded cDNA is made up. Since this double-stranded cDNA comprises T7 promoter sequence, if T7 RNA polymerase is allowed to act on this, RNA (antisense strand) is formed successively by transcription. Furthermore, as to the double-stranded cDNA formed, by repeating a denaturation process, an annealing process with the above-described forward primer and the reverse primer, and an extension process of complementary strand, the double-stranded cDNA is amplified, and further, by the transcription using this as a template, RNA (antisense strands) is also formed. In such NASBA method, only alternative splicing variant can also be amplified by employing the above-described primer as one primer (in this regard, however, the product is antisense strands as described above). In addition, the NASBA method in itself is well-known technology, and since the kit for it is also commercially available, it can be easily carried out employing the kit in the market.

Other preferable methods for measuring an alternative splicing variant by detecting the presence of exon SV as an indicator include a method in which a probe capable of hybridizing with the region comprising this exon SV under a stringent condition is employed (in situ hybridization method). As for the probe, the one which is capable of hybridizing with the exon SV region in the nucleic acid having nucleotide sequence represented by SEQ ID NO: 1 under a stringent condition, but does not hybridize with the nucleic acid having nucleotide sequence represented by SEQ ID NO: 2 is employed. In order to ensure such specificity, preferable probe is the one in which 20 to 80% of the entire length of the probe, more preferably 40 to 60% of the entire length of the probe hybridizes with the exon SV region under a stringent condition, and the rest portion of the probe hybridizes with adjacent exon 3 region under a stringent condition. Size of the probe is not particularly limited, however, in the case of an oligonucleotide, it is usually 10 nucleotides to the entire length, preferably about 10 nucleotides to about 100 nucleotides, and further preferably about 15 nucleotides to about 35 nucleotides, and in the case of cRNA or cDNA, it is usually 300 nucleotides to 800 nucleotides. In addition, as is the case of primer, it is extremely preferable as a probe to have completely the same nucleotide sequence as the region to where the probe hybridizes, however, 10% or less of nucleotides of full length probe may be replaced.

The probe may be modified to a labeled probe by binding well-known labels, such as fluorescent label, biotin label, radiation label, and an enzyme label to the above-described nucleic acid. In addition, in the case where the probe is used as a solid-phased probe, the probe may be the one which has been coupled with any nucleic acid irrelevant to the test nucleic acid, such as the region to be attached to the solid phase, or a branch in the branched probe for binding with the label.

Probe can be used for a direct measurement of mRNA of alternative splicing variant contained in the sample to be examined, and also for the purpose of measuring amplified nucleic acid, after the mRNA is amplified by the nucleic acid amplification method such as the RT-PCR. When amplification product is specifically measured with a probe, to amplify a nucleic acid, primer is set so that exon SV is contained in amplification products. The primer, in this case, is not necessary to be specific to the alternative splicing variant, but the measurement specificity is secured by the probe.

The present invention also provides a nucleic acid which is capable of hybridizing with the nucleic acid comprising the nucleotide sequence represented by SEQ ID NO: 1, and even if the nucleic acid comprising the nucleotide sequence represented by SEQ ID NO: 2 is coexisted, does not hybridize with such nucleic acid; or the nucleic acid which, even if hybridization takes place with the nucleic acid comprising the nucleotide sequence represented by SEQ ID NO: 2, the 3' terminal thereof becomes mismatched. Such nucleic acids can be used as a primer and a probe mentioned above. As such nucleic acids, the nucleic acids which are capable of hybridizing with the region comprising exon SV in the nucleotide sequence represented by SEQ ID NO: 1, and even if the nucleic acid comprising the nucleotide sequence represented by SEQ ID NO: 2 is coexisted, does not hybridize, or the nucleic acid which, when hybridization takes place with the nucleic acid comprising the nucleotide sequence represented by SEQ ID NO: 2, the 3' terminal thereof becomes mismatched, are preferable for the specific measurement of alternative splicing variant. Such nucleic acids of the present invention have the number of nucleotide of preferably 10 or more, and particularly preferably 15 to 35. In addition, the nucleic acids of the present invention preferably have the same nucleotide sequence as the nucleotide sequence represented by SEQ ID NO: 1 or partial region thereof, or the nucleotide sequence in which 10% or less of nucleotides of the aforementioned nucleotide sequence are replaced, and particularly preferably is consisted of the same nucleotide sequence as the nucleotide sequence represented by SEQ ID NO: 1 or partial region thereof.

Such nucleic acid of the present invention can be used as a nucleic acid for the measurement of alternative splicing variant such as a primer or a probe of the nucleic acid amplification method.

Further, the present invention also provides a measurement kit for alternative splicing variant of OATP1B3 mRNA comprising the above described nucleic acid for measurement of the present invention. Except for the nucleic acid for measurement of the present invention, the reagents contained in the kit may be known substances, and the measurement kit can be made up by comprising, for example, in addition to a primer set, reverse transcriptase, Taq DNA polymerase, dNTP, random primer, RNase inhibitor, buffer solution, and the like. Alternatively, the kit may be made up of the primer set which consists only of a forward primer and a reverse primer, and as for other reagents, a commercial kit for RT-PCR or the like may be utilized.

The alternative splicing variant mentioned above can be used as a tumor marker. That is, it has been clarified that the alternative splicing variant provided by the present invention is expressed specifically and strongly in cancer cell and tissue. Therefore, the measurement method and the measurement kit provided by the present invention can be applied for the detection of cancer. In this regard, type of cancer of detection target is not particularly limited, and can be used, for example, for the detection of colon cancer, pancreatic cancer, breast cancer, lung cancer, prostatic cancer, esophageal cancer, stomach cancer, liver cancer, biliary tract carcinoma, spleen cancer, renal carcinoma, bladder cancer, uterine cancer, ovarian cancer, testicular cancer, thyroid cancer, brain tumor, hematopoietic tumor, and the like. Particularly, as is described in Example mentioned later, it has been confirmed that the OATP1B3/ct is expressed strongly, not only in the human colon cancer tissue, also in the cell line derived from human colon cancer (LS180, HCT116) and in the cell line derived from human pancreatic cancer (PK45p). On the other hand, since the expression of OATP1B3/ct was not confirmed in the tissue of normal human colon origin, the alternative splicing variant provided by the present invention is particularly useful as a marker of colon cancer and pancreatic cancer.

According to another aspect of the present invention, there is provided a method for screening preventive and/or therapeutic agent for cancer. In this screening method, firstly the cancer cell is cultured in the presence of a test substance. And, for the cultured cell obtained, the above-described alternative splicing variant of the present invention is measured. Subsequently, the obtained measurement results are compared with the results of the case where the above-described test substance is absent and/or evaluated.

Specifically, cancer cell lines derived from various types of carcinoma as described above are cultured in the presence of test substance such as anticancer drug, candidate anticancer substance, low molecular weight compound, natural organic polymer substance, extract from natural animals and plants, and peptide; and the alternative splicing variant of the present invention in the aforementioned cultured cell is measured (detected, measured semi-quantitatively, measured quantitatively); and when the form of the alternative splicing variant is decreased significantly compared with the case where the test substance is absent, it is judged that the test substance can be useful as a preventive and/or therapeutic agent for the cancer from which the above-described cell line has been derived.

In the screening method of the present invention, screening of a preventive and/or therapeutic agent for human colon cancer can be performed by using the cell line derived from human colon cancer (for example, LS180 and HCT116). Similarly, screening of preventive and/or therapeutic agent for human pancreatic cancer can be performed by using the cell line derived from human pancreatic cancer (for example, PK45p). With respect to the cell lines derived from other well-known cancers and tumors, by using the cell lines similarly, screening of preventive and/or therapeutic agents for various types of cancers and tumors can be performed.

In addition, in the screening method of the present invention, as for the method for measuring an alternative splicing variant, the above-described measurement method and the measurement kit of the present invention can be used similarly. Therefore, detailed description is omitted here.

According to the studies carried out by the inventors of the present invention, it became clear that at least 4 kinds of polypeptides might be expressed from OATP1B3/ct mRNA. Specifically, it was confirmed that the polypeptides consisting of respective amino acid sequences represented by SEQ ID NO: 5, SEQ ID NO: 7, SEQ ID NO: 9, and SEQ ID NO: 11, respectively, may be expressed from OATP1B3/ct mRNA. These polypeptides are unable to be expressed theoretically from OATP1B3/wt mRNA, and are specific for OATP1B3/ct mRNA. For this reason, these polypeptides have usefulness as a tumor marker like OATP1B3/ct mRNA.

From the viewpoint mentioned above, according to another aspect of the present invention, there are provided the following polypeptides:

(1) a polypeptide which consists of an amino acid sequence represented by SEQ ID NO: 5, SEQ ID NO: 7, SEQ ID NO: 9, or SEQ ID NO: 11; and (2) a polypeptide which comprises an amino acid sequence represented by SEQ ID NO: 5, SEQ ID NO: 7, SEQ ID NO: 9, or SEQ ID NO: 11, and expression of which is enhanced in cancer cell or cancer tissue, or else, a polypeptide which comprises an amino acid sequence represented by SEQ ID NO: 5, SEQ ID NO: 7, SEQ ID NO: 9, or SEQ ID NO: 11 in which 10% or less of the amino acids are replaced, deleted and/or inserted, and expression of which is enhanced in cancer cell or cancer tissue (also, referred to as "functionally equivalent variant").

"(2) Functionally equivalent variant" includes "a polypeptide which comprises an amino acid sequence represented by SEQ ID NO: 5, SEQ ID NO: 7, SEQ ID NO: 9, or SEQ ID NO: 11, and expression of which is enhanced in cancer cell or cancer tissue", or "a polypeptide which comprises an amino acid sequence represented by SEQ ID NO: 5, SEQ ID NO: 7, SEQ ID NO: 9, or SEQ ID NO: 11 in which 0 to 10%, preferably 0 to 7%, further more preferably 0 to 5%, and particularly preferably 0 to 2% of the amino acids are replaced, deleted and/or inserted, and expression of which is enhanced in cancer cell or cancer tissue".

"Expression of which is enhanced in cancer cell or cancer tissue" means that expression is enhanced by 2 folds or more in cancer cell or cancer tissue as compared with the case in non-cancer cell or non-cancer tissue.

As mentioned above, although polypeptides of the present aspect were explained, hereinafter, the polypeptide which consists of amino acid sequences represented by SEQ ID NO: 5, SEQ ID NO: 7, SEQ ID NO: 9, or SEQ ID NO: 11, and the above-described functionally equivalent variant thereof are also referred to collectively as "polypeptides of the present invention". In addition, among the "polypeptides of the present invention", the polypeptide consisting of amino acid sequence represented by SEQ ID NO: 5 is referred to as "f1-1", the polypeptide consisting of amino acid sequence represented by SEQ ID NO: 7 is referred to as "f1-2", the polypeptide consisting of amino acid sequence represented by SEQ ID NO: 9 is referred to as "f2", the polypeptide consisting of amino acid sequence represented by SEQ ID NO: 11 is referred to as "f3", respectively.

As the polypeptide of the present invention, f1-1 or f3 is particularly preferable.

According to still another aspect of the present invention, there are also provided nucleic acids which encode the polypeptides of the present invention.

Here, the nucleic acid consisting of nucleotide sequence which encodes the f1-1 of the polypeptide of the present invention is not particularly limited, as long as it is the nucleotide sequence which encodes f1-1 consisting of amino acid sequence represented by SEQ ID NO: 5 or functionally equivalent variant thereof. Preferably, it is the nucleic acid consisting of nucleotide sequence which encodes amino acid sequence represented by SEQ ID NO: 5; and further more preferably, it is the nucleic acid consisting of nucleotide sequence represented by SEQ ID NO: 4.

Similarly, the nucleic acid consisting of nucleotide sequence which encodes the f1-2 of the polypeptide of the present invention is not particularly limited, as long as it is the nucleotide sequence which encodes f1-2 consisting of amino acid sequence represented by SEQ ID NO: 7 or functionally equivalent variant thereof. Preferably, it is the nucleic acid consisting of nucleotide sequence which encodes amino acid sequence represented by SEQ ID NO: 7; and further more preferably, it is the nucleic acid consisting of nucleotide sequence represented by SEQ ID NO: 6.

In addition, the nucleic acid consisting of nucleotide sequence which encodes the f2 of the polypeptide of the present invention is not particularly limited, as long as it is the nucleotide sequence which encodes f2 consisting of amino acid sequence represented by SEQ ID NO: 9 or functionally equivalent variant thereof. Preferably, it is the nucleic acid consisting of a nucleotide sequence which encodes amino acid sequence represented by SEQ ID NO: 9; and further more preferably, it is the nucleic acid consisting of the nucleotide sequence represented by SEQ ID NO: 8.

In addition, the nucleic acid consisting of nucleotide sequence which encodes the f3 of the polypeptide of the present invention is not particularly limited, as long as it is the nucleotide sequence which encodes f3 consisting of amino acid sequence represented by SEQ ID NO: 11 or functionally equivalent variant thereof. Preferably, it is the nucleic acid consisting of nucleotide sequence which encodes amino acid sequence represented by SEQ ID NO: 11; and further more preferably, it is the nucleic acid consisting of nucleotide sequence represented by SEQ ID NO: 10.

In addition, according to another aspect of the present invention, there are also provided an expression vector comprising the above-described nucleic acids, a cell which has been transformed by the aforementioned expression vector.

The expression vector and the cell of the present invention can be produced by referring to well-known knowledge of prior art. For example, a host cell of eukaryotes or prokaryotes can be transformed by incorporating isolated nucleic acid of the present invention into an appropriate vector DNA once again. In addition, it is possible for respective host cells to express the nucleic acid by introducing an appropriate promoter and a sequence relevant to the expression of phenotype into these vectors.

The expression vector of the present invention is not particularly limited, as long as the nucleic acid of the present invention is contained, and, for example, the expression vector obtained by inserting the nucleic acid of the present invention into a known expression vector selected appropriately according to the host cell to be employed is included.

In addition, the cell of the present invention may be, but not limited particularly as long as the cell is transfected with the vector of the present invention and comprises the nucleic acid of the present invention, for example, the cell which has been incorporated with the nucleic acid of the present invention into chromosome of the host cell, or the cell which comprises the nucleic acid of the present invention in the form of expression vector. Moreover, it may be a cell which is expressing the polypeptide of the present invention, or may be a cell which is not expressing the polypeptide of present invention. The cell of the present invention can be obtained, for example, by transfecting expression vector of the present invention into a desired host cell.

The desired cell obtained as described above can be cultured according to the conventional method, and the polypeptide of the present invention is produced by the aforementioned culture. As for the medium to be employed for the aforementioned culture, various kinds of medium commonly used depending on the adopted host cell are selected appropriately.

According to the above description, the polypeptide of the present invention produced by the transformed cell can be isolated and purified by various kinds of well-known separation procedures through the use of physical property, biochemical characteristics, etc. of the polypeptide.

By way of expression after making the marker sequence fused in-frame, it becomes possible to confirm its expression, to purify it, and so on. The marker sequence includes, for example, FLAG epitope, Hexa-Histidine tag, Hemagglutinin tag, myc epitope, etc. In addition, by inserting a specific amino acid sequence which can be recognized by a protease such as enterokinase, factor Xa, thrombin and the like in between the marker sequence and polypeptide, it is also possible to remove the marker sequence part by cutting with these enzymes.

The nucleic acid of the present invention, in itself or a part thereof can be used as a hybridization probe in the method for detecting cancer, and so, these are useful for the detection of cancer. In addition, the polypeptide of the present invention can be used for the preparation of specific antibody for recognizing the polypeptide of the present invention, and as a control in the detection and quantitative measurement of expression level.

According to the present invention, the antibody which binds to the polypeptide of the present invention (hereafter, also referred to as "the antibody of the present invention") can also be provided. The manufacturing method of the antibody of the present invention is not particularly limited. The antibody of the present invention (for example, polyclonal antibody, monoclonal antibody) can be obtained, for example, by direct administration of the polypeptide which comprises an amino acid sequence represented by SEQ ID NO: 5, and the expression of which is enhanced in cancer cell or cancer tissue, or the polypeptide which comprises an amino acid sequence represented by SEQ ID NO: 5 in which 1 or several amino acid is replaced, deleted and/or inserted, and the expression of which is enhanced in cancer cell or cancer tissue, or the entire of the polypeptide or fragment thereof which consists of the amino acid sequence represented by SEQ ID NO: 5 into various animals. Also, by the method of DNA vaccination using a plasmid which has been introduced with the gene encoding the above described polypeptide, the antibody can be obtained (Raz, E. et al., Proc. Natl. Acad. Sci. USA, 91, 9519-9523, 1994; Donnelly, J. J. et al., J. Infect. Dis., 173, 314-320, 1996).

Polyclonal antibody is produced by emulsifying the aforementioned polypeptide or fragment thereof in a suitable adjuvant such as Freund's complete adjuvant, and administering the emulsion to animal, for example, rabbit, rat, goat, or it) chicken, through intraperitoneal, subcutaneous or intravenous route to immunize, then obtaining the polyclonal antibody from serum or egg of such sensitized animal. The polyclonal antibody produced in this way can be isolated and purified by the conventional protein isolation and purification method. The conventional protein isolation and purification method includes, for example, centrifugal separation, dialysis, salting out by ammonium sulfate, DEAE cellulose, hydroxyapatite, and chromatographic procedures by protein A agarose and the like.

Monoclonal antibody can be easily produced by the person skilled in the art according to the cell fusion method described by Kohler and Milstein (Kohler, G. and Milstein, C., Nature, 256, 495-497, 1975).

According to still another aspect of the present invention, there is also provided a nucleic acid which is capable of hybridizing with the nucleic acid comprising the nucleotide sequence represented by SEQ ID NO: 4, SEQ ID NO: 6, SEQ ID NO: 8, or SEQ ID NO: 10 under a stringent condition, and has at least 15 nucleotides. The "stringent condition" is as mentioned above. Such nucleic acid can be used as a probe for detecting and for isolating the nucleic acid of the present invention, and also as a primer for amplifying the nucleic acid of the present invention. In the case where it is used as a primer, chain length is usually 15 bp to 100 bp, and preferably 15 bp to 40 bp. Preferable nucleotide sequence as a primer includes nucleotide sequence of the primer used for amplifying each of f1-1, f1-2, f2 and f3 in "9. Preparation of expression plasmid for green fluorescent protein (GFP) fusion ctOATP1B3 peptide" described later in Example. Further, in the case where it is used as a probe, a DNA which has a part of or whole sequence (or complementary sequence thereof) of the nucleic acid of the present invention and a chain length of at least 15 bp is employed.

A probe and a primer employing the above described nucleic acid can be used for detection of cancer.

In addition, based on the present invention, an array of the oligonucleotide probe comprising the nucleotide sequence of the nucleic acid of the present invention or fragment thereof can also be constructed. Array technique is well-known, and has been used for analyzing gene expression (Chee, M. et al., (1996) Science, 274, 610-613).

The polypeptide of the present invention can also be applied to a method for detecting cancer. That is, according to another aspect of the present invention, there is provided a method for detecting cancer comprising measuring the amount of the polypeptide of the present invention in a sample to be examined which is isolated from living organism. On this occasion, it is preferable to employ the aforementioned antibody of the present invention. In addition, a detection kit for cancer comprising the aforementioned antibody can also be provided. Hereinafter, this embodiment will be explained in more detail.

Detection of the polypeptide of the present invention in a sample to be examined can be performed, for example, by subjecting the sample to be examined to a method constructed by combining various molecular weight measurement methods such as gel electrophoresis, various kinds of separation and purification methods (e.g. ion exchange chromatography, hydrophobic chromatography, affinity chromatography, reverse phase chromatography, and the like), ionization methods (e.g. electron impact ionization method, field desorption method, secondary ionization method, fast atom bombardment method, matrix assisted laser desorption/ionization (MALDI) method, electrospray ionization method, and the like), and mass spectrometers (e.g. double-focusing mass spectrometer, quadrupole mass spectrometer, time-of-flight mass spectrometer, Fourier transform mass spectrometer, ion-cyclotron mass spectrometer, and the like), and by detecting a band or a spot, or a peak corresponding to the molecular weight of the polypeptide of the present invention, but is not limited thereto. Since the amino acid sequence of the polypeptide of the present invention is known, a method for detecting the polypeptide of the present invention by preparing an antibody which recognizes the aforementioned amino acid sequence, and carrying out western blotting or various immunoassays using the antibody can be employed more preferably. In addition, the method for preparing the aforementioned antibody is as mentioned above. The detection method for the polypeptide of the present invention using the antibody of the present invention is particularly useful in that the polypeptide of the present invention can be detected with high sensitivity and preciseness without employing special equipment like mass spectrometer, if an optimized immunoassay system is developed and constructed as a kit.

The detection method for cancer of the present invention using the antibody of the present invention is not particularly limited, and any measurement method can be employed, as long as it is a measurement method in which the amount of antibody, antigen or antibody-antigen complex corresponding to the amount of antigen in the sample to be examined is detected by chemical or physical procedures, and computed from a standard curve which is made using standard solutions containing known amounts of the antigen. For example, nephelometry, competition method, immunometric method, sandwiching method, and the like are used suitably.

As to a labeling agent to be used in the measurement method using a labeling substance, for example, radioisotope, enzyme, fluorescent substance, luminescent substance, and the like are employed. As to radioisotope, for example, [125I], [131I], [3H], [14C], and the like are used. As to the above-described enzyme, the one which is stable and has a high specific activity is preferable, and, for example, β-galactosidase, β-glucosidase, alkaline phosphatase, peroxidase, malate dehydrogenase, and the like are used. As to fluorescent substance, for example, fluorescamine, fluorescein isothiocyanate, and the like are used. As to luminescent substance, for example, luminol, luminol derivatives, luciferin, lucigenin, and the like are used. Furthermore, biotin-avidin system can also be employed for binding of antibody or antigen and labeling agent.

For the purpose of insolubilization of antigen or antibody, physical adsorption may be used, or a method using chemical bond which is usually used for insolubilizing or immobilizing protein or enzyme may be used. The carrier includes insoluble polysaccharides such as agarose, dextran, and cellulose, synthetic resin such as polystyrene, polyacrylamide, and silicone, or glass, and so on.

In the sandwich technique, the insolubilized antibody of the present invention is reacted with the sample to be examined (primary reaction), and further reacted with labeled another antibody of the present invention (secondary reaction), after that, an amount (activity) of the labeling agent on the insolubilized carrier is measured, and thereby an amount of the peptide of the present invention in the sample to be examined can be measured quantitatively. The primary reaction and the secondary reaction may be carried out in reverse order, or may be performed simultaneously or with a certain interval.

The monoclonal antibody against the polypeptide of the present invention can also be used for measurement system other than the sandwich technique, for example, the competition method, the immunometric methods, or the nephelometry, and so on.

In the competition method, after reacting the antigen in a sample to be examined and the labeled antigen competitively with the antibody, unreacted labeled antigen (F) and labeled antigen (B) bound with the antibody are separated (B/F separation), and the amount of label of either B or F is measured, to determine the amount of the antigen in the sample to be examined. For this reaction method, liquid phase method in which a soluble antibody is used as the antibody, and B/F separation is carried out using polyethylene glycol and a secondary antibody against the aforementioned antibody, and the like, and solid phase method in which a solid-phased antibody is used as a primary antibody, or a soluble antibody is used as a primary antibody and a solid-phased antibody is used as the secondary antibody, are employed.

In the immunometric method, after the antigen in the sample to be examined and the solid-phased antigen are reacted competitively with a certain amount of labeled antibody, the solid phase and the liquid phase are isolated, or else, the antigen in the sample to be examined is reacted with an excess amount of labeled antibody, then the solid-phased antigen is added to bind unreacted labeled antibody to the solid phase, after that the solid phase and the liquid phase are separated. Subsequently, an amount of label of any phase is measured, to determine the amount of antigen in the sample to be examined quantitatively.

In addition, in the nephelometry, the amount of the insoluble sediment produced within gel or in solution as a result of the antigen-antibody reaction is measured. Even when the amount of antigen in the sample to be examined is small, and only a small amount of sediment is obtained, a laser nephelometry using dispersion of laser and the like is employed suitably.

In applying these respective immunological measurement methods to the detection method of the present invention, any setup of particular conditions, operations, and the like is not required. The measurement system for the polypeptide of the present invention may be constructed by adding the usual technical considerations of those skilled in the art to the usual conditions and operations in the respective methods. As to the details of these general technical procedures, review articles, books, etc. can be referred to. For example, Hiroshi Irie ed., "Radioimmunoassay" (Kodansha, published in Showa 49); Hiroshi Irie ed., "Continued Radioimmunoassay" (Kodansha, published in Showa 54); Eiji Ishikawa, et al. ed., "Enzyme-Linked Immunosorbent Assay" (Igaku-Shoin, published in Showa 53); Eiji Ishikawa, et al. ed., "Enzyme-Linked Immunosorbent Assay", (2nd Edition) (Igaku-Shoin, published in Showa 57); Eiji Ishikawa, et al. ed., "Enzyme-Linked Immunosorbent Assay", (3rd Edition) (Igaku-Shoin, published in Showa 62); "Methods in ENZYMOLOGY" Vol. 70 (Immunochemical Techniques (Part A)), ibid. Vol. 73 (Immunochemical Techniques (Part B)), ibid. Vol. 74 (Immunochemical Techniques (Part C)), ibid. Vol. 84 (Immunochemical Techniques (Part D: Selected Immunoassays)), ibid. Vol. 92 (Immunochemical Techniques (Part E: Monoclonal Antibodies and General Immunoassay Methods)), ibid. Vol. 121 (Immunochemical Techniques (Part I: Hybridoma Technology and Monoclonal Antibodies)) (the foregoing are published from Academic Press), etc. can be referred to.

Alternatively, another detection method for the present invention using the antibody of the present invention includes a method in which the aforementioned antibody is fixed on the surface of the probe which can conform to the aforementioned mass spectrometer; a sample to be examined is allowed to contact with the aforementioned antibody on the aforementioned probe; and the biological sample component caught by the aforementioned antibody is subjected to mass spectrometry; to detect a peak corresponding to the molecular weight of the marker peptide which is recognized by the aforementioned antibody.

When the polypeptide of the present invention is detected in a sample to be examined with statistically significant difference from the level in the control sample by any one of the above described methods, it can be diagnosed that possibility of comprising cancer cell or cancer tissue in the sample to be examined is high.

According to still another aspect of the present invention, a medicament is provided. The aforementioned medicament comprises the above-described polypeptide of the present invention or fragment thereof, or the nucleic acid of the present invention or fragment thereof, which is to be used for inducing specific cytotoxic T-cell (CTL). The aforementioned medicament is preferably cancer vaccine. Hereafter, this embodiment will be explained in more detail.

When the medicament of the present invention comprises the polypeptide of the present invention or fragment thereof, it is necessary that the aforementioned polypeptide or fragment thereof can induce specific cytotoxic T-cell (CTL) by binding with HLA. From this point of view, it is preferable that the aforementioned polypeptide or fragment thereof consists of consecutive 8 to 11 amino acid residues in the polypeptide of the present invention. It should be noted that the polypeptide fragment inducing specific CTL can easily be prepared by referring to the well-known knowledge in the art.

"Can induce specific cytotoxic T-cell (CTL) by binding with HLA" means that the polypeptide of the present invention or fragment thereof, or the nucleic acid of the present invention or fragment thereof forms a complex by binding with HLA, and such complex can be recognized by the CTL. In other words, it means that the polypeptide of the present invention or fragment thereof, or the nucleic acid of the present invention or fragment thereof has binding activity with HLA, and has an activity to induce a specific CTL in the form of a complex with HLA.

On the other hand, when the medicament of the present invention comprises the nucleic acid of the present invention or fragment thereof, the polypeptide which has an amino acid sequence encoded by the aforementioned nucleic acid is recognized in itself by CTL, and can activate the aforementioned CTL, or can provide a polypeptide fragment having such activity, and can function as a tumor antigen. As for the nucleic acid or fragment thereof employed in the present aspect, it is preferable that they are the polynucleotide or complementary strand thereof which consists of at least 24 or more of nucleotides corresponding to the region coding the polypeptide of the present invention. Such a polynucleotide can be selected by checking the expressed peptides, for example, using known protein expression system.

The medicament of the present invention can be used, for example, as a cancer vaccine. Although only one kind of polypeptide or fragment thereof, or nucleic acid or fragment thereof is effective as a cancer vaccine, it is preferable that plural kinds of them are used in combination. This is because it is expected to be more effective to use plural types of tumor antigens in combination as a vaccine, because CTL of cancer patients is a cell population which recognizes several different kinds of tumor antigens. In addition, the polypeptide of the present invention and the nucleic acid of the present invention may be used in conjunction with a polypeptide or a nucleic acid other than these.

The cancer vaccine provided by the present invention can be used in the presence or absence of an appropriate adjuvant, independently or by binding with pharmaceutically acceptable carrier. The carrier is not particularly limited as long as it does not give any hazardous effect on human body, and, for example, cellulose, polymerized amino acid, albumin, and the like can be used. As to dosage form, the dosage form which is well known for peptide formulation can be selected. As to dosage, it may vary depending on the recognition property of CTL, disorder to be treated, age of patient, body weight and so on, however, in the case of peptide, it is usually 0.0001 mg to 1000 mg/day/adult human, preferably 0.001 mg to 1000 mg/day/adult human, more preferably 0.1 mg to 100 mg/day/adult human, further more preferably 0.1 mg to 10 mg/day/adult human as an active entity. This medication may be administered once a day, once a week, or once several months.

The medicament of the present invention can also be utilized for incorporating the polypeptide of the present invention or fragment thereof into an appropriate vector, and for introducing the vector in vivo or ex vivo. The vector includes, for example, retrovirus, adenovirus, vaccinia virus, and the like, and retroviral system is preferable. Dosage may vary depending on the recognition property of CTL, however, it is 0.1 μg to 100 mg/day/adult human, and preferably 1 μg to 50 mg/day/adult human, as a DNA content. This medication may be administered once a day, once a week, or once several months.

Examples

Hereinafter, the present invention will be explained more specifically by means of Examples and Reference Examples, however, technical scope of the present invention shall not be limited thereto.

1. Primer

The primers used for genomic DNA contamination check, RNA ligase-mediated rapid amplification of 5'cDNA end (RLM-RACE), reverse transcription PCR (RT-PCR), cDNA cloning, quantitative real-time PCR, and the primers used for peptide expression from the GFP fusion peptide expression plasmid were synthesized by Invitrogen (Carlsbad, Calif., USA) or Greiner-Bio-One (Taufkirchen, Germany) on consignment contract, and each of them has nucleotide sequence shown in Tables 1 to 6 below.

TABLE 1

Primer Used for Genomic DNA Contamination Check

| Primer | Nucleotide sequence (5'→3') |
|---|---|
| GAPDH F | TGCACCACCAACTGCTTA (SEQ ID NO: 12) |
| GAPDH R | GGATGCAGGGATGATGTTC (SEQ ID NO: 13) |

F: forward ; R: reverse

TABLE 2

Primer Used for RLM-5'-RACE

| Primer | Nucleotide sequence (5'→3') |
|---|---|
| SLCO1B3 648R | GCCACGAAGCATATTCCCCATGAAG (SEQ ID NO: 14) |
| SLCO1B3 424Rnest | TTCCAGTTCCCATAAGGAGACAACC (SEQ ID NO: 15) |

R: reverse

TABLE 3

Primer Used for RT-PCR

| Primer | Nucleotide sequence (5'→3') | Annealing temperature (° C.) |
|---|---|---|
| SLCO1B3TSS in cancer 33F | GTGCAAGTCACAGGGGATGG GA (SEQ ID NO: 16) | 60 |
| SLCO1B3TSS in cancer 145R | GCTGAATGACAGGGCTGCCA AG (SEQ ID NO: 17) | 60 |

F: forward; R: reverse

TABLE 4

Primer Used for cDNA Cloning of OATP1B3/ct and OATP1B3/wt

| Primer | Nucleotide sequence (5'→3') |
|---|---|
| ctSLCO1B3 cloning F33 | GTGCAAGTCACAGGGGATGGGA (SEQ ID NO: 16) |
| ctSLCO1B3 cloning 2149R | GCAATGTTAGTTGGCAGCAGCA (SEQ ID NO: 18) |
| SLCO1B3 F27 | GGTATCTGTAGTTTAATAATGGACC (SEQ ID NO: 19) |
| SLCO1B3 R2184 | GAAAGACCAGGAACACCTCA (SEQ ID NO: 20) |

TABLE 5

Primer Used for Quantitative Real-Time PCR

| Primer | Nucleotide sequence (5'→3') |
|---|---|
| ctSLCO1B3 Left 59-76 | TTGGCTTGGGCTCAGAGA (SEQ ID NO: 21) |
| ctSLCO1B3 Right 130-151 | TGCCAAGAACATCTGCTAGTTT (SEQ ID NO: 22) |
| SLCO1B3 F153 for real-time | AACAGCAGAGTCAGCATCTTCAG (SEQ ID NO: 23) |
| SLCO1B3 R194 for real-time | AACATCTTGAATCCATTGCAGC (SEQ ID NO: 24) |

F: forward ; R: reverse

TABLE 6

Primer Used for Peptide Expression from the GFP Fusion Peptide Expression Plasmid

| Primer | Nucleotide sequence (5'→3') |
|---|---|
| Frame 1-1 | |
| ct1B3 f1 45-78 + GFP | CCtctagaGGGATGGGATGGCTTGGCTTGGGCTCAGAGACCGTGA GCAAGGGCG (SEQ ID NO: 25) |
| GFP L696 + KpnI | GGggtaccTTACTTGTACAGCTCATCCATGCCG (SEQ ID NO: 26) |
| Frame 1-2 | |
| ctOATP1B3 cloning U33 + XbaI | GCtctagaGTGCAAGTCACAGGGGATGGGA (SEQ ID NO: 27) |
| ct1B3 f1 L153 + BamHI | GTggatccGCAATATAGCTGAATGACAGGG (SEQ ID NO: 28) |
| Frame 2 | |
| ctOATP1B3 cloning U33 + XbaI | GCtctagaGTGCAAGTCACAGGGGATGGGA (SEQ ID NO: 27) |
| ct1B3 f2 L239 + BamHI | TAggatccACCAGCAAGAGAAGAGGA (SEQ ID NO: 29) |
| Frame 3 | |
| ctOATP1B3 cloning U33 + XbaI | GCtctagaGTGCAAGTCACAGGGGATGGGA (SEQ ID NO: 27) |
| ct1B3 f3 L160 + BamHI | TCggatccGTGCTTTAGCAATATAGCTGAAT (SEQ ID NO: 30) |
| GFP | |
| GFP U4 + BamHI | CGggatccGTGAGCAAGGGCGCCGAGC (SEQ ID NO: 31) |
| GFP L696 + KpnI | GGggtaccTTACTTGTACAGCTCATCCATGCCG (SEQ ID NO: 32) |

*Lower-cases indicate recognition sites of restriction enzymes.

2. Cell Culture Method

LS180 cell which is a cell line derived from human colon cancer was purchased from Dainippon Sumitomo Pharma Co. Ltd. (Osaka, Japan). HCT116 cell which is a cell line derived from human colorectal cancer was kindly bestowed from Dr. Vogelstein (Johns Hopkins University, Baltimore, Md., USA). PK45p cell which is a cell line derived from human pancreatic cancer was obtained from Cell Resource Center for Biomedical Research, Institute of Development, Aging and Cancer, Tohoku University (Sendai, Japan). LS180 cell and PK45p cell were each cultured in Minimum Essential Medium (MEM) (Invitrogen) or RPMI (Roswell Park Memorial Institute) 1640 medium (Invitrogen) supplemented with 10% heat-inactivated fetal bovine serum (FBS) (Gemini Bio-Products, CA, USA), and 50 U/mL penicillin-50 μg/mL streptomycin (Invitrogen), in an atmosphere of 5% $CO_2$/95% air, at 37° C. in a $CO_2$ incubator.

3. Experimental Sample

Caucasian liver sample was obtained from the HAB (Human and Animal Bridging) Research Organization (Tokyo, Japan). The above-described sample is transplantation-incompatible human liver tissue which was imported from the U.S. through National Disease Research Interchange (NDRI) (Philadelphia, Pa., USA). In addition, the above-described liver tissue used was not suffered from infectious diseases such as hepatitis. In addition, the research use of these specimens in the present studies was approved in advance by the Ethics Committee, Graduate School of Pharmaceutical Sciences, Chiba University.

4. Extraction of Total RNA

Extraction of total RNA from cell was performed using FastPure™ RNA Isolation Kit (Takara Bio Inc., Shiga, Japan) according to the protocol. No contamination of genomic DNA in the extracted total RNA was confirmed by the PCR employing 20 μL of reaction solution which contains 10 μL of GoTaq Green Master Mix (Promega Corporation, Madison, Wyo., USA) and each 0.5 μL of primers (human glyceraldehyde-3-phosphate dehydrogenase (GAPDH) F and GAPDH R, as shown in the above Table 1), and 1 μL of RNA. The PCR was carried out as follows: after heating the reaction solution at 95° C. for 30 seconds, a reaction cycle composed of heating at 95° C. for 10 seconds, at 50° C. for 10 seconds and at 72° C. for 30 seconds was repeated for 40 times. Also, the extraction of the total RNA from the Caucasian liver was carried out according to the protocol using FastPure™ RNA Isolation Kit. A pair of cancerous/normal colon total RNA was purchased from Applied Biosystems Inc. (Foster city, MA, USA).

5. Determination of Transcription Starting Point of SLCO1B3 Gene

Transcription starting point of SLCO1B3 gene was determined by the RLM-5'-RACE method using GeneRacer™ Kit (Invitrogen). The determination was performed using the total RNA derived from human colorectal cancer or the total RNA derived from Caucasian liver as a template according to the protocol. For the PCR reaction, a 20 μL of PCR reaction solution containing 10 μL of GoTaq Green Master Mix, 1 μL of reverse transcriptase template, and each 0.5 μL of 10 μM GeneRacer™ 5'primer and reverse gene specific primer ("SLCO1B3 648R", as shown in the above Table 2) was prepared. After heating the reaction solution at 94° C. for 2 minutes, Touch-down PCR in which a reaction cycle composed of heating at 94° C. for 30 seconds, at 68° C. for 30 seconds and at 72° C. for 1 minute was repeated 5 times; a reaction cycle composed of heating at 94° C. for 30 seconds, at 66° C. for 30 seconds and at 72° C. for 1 minute was repeated 5 times; a reaction cycle composed of heating at 94° C. for 30 seconds, at 65° C. for 30 seconds and at 72° C. for 1 minute was repeated 30 times were carried out consecutively, was performed. After this Touch-down PCR, Nested-PCR was performed using the PCR reaction solution diluted 5 times with sterile water as a template. For the Nested-PCR reaction, 20 μL of PCR reaction solution containing 10 μL of GoTaq Green Master Mix, 1 μL of template, and each 0.5 μL of 10 μM GeneRacer™ 5'Nested primer and reverse Nested gene specific primer ("SLCO1B3 424Rnest", as shown in the above Table 2) was prepared. After heating this reaction solution at 95° C. for 30 seconds, a reaction cycle composed of heating at 95° C. for 10 seconds, at 53° C. for 10 seconds and at 72° C. for 30 seconds was repeated for 40 times. The PCR products was subjected to 3% agarose gel electrophoresis, and visualized by ethidium bromide staining. Results of the electrophoresis are shown in FIG. 3. As shown in FIG. 3, with the sample obtained by using total RNA derived from Caucasian liver as a template, a band corresponding to the reported transcription starting point ("TSS" as shown in FIG. 1) was confirmed. On the other hand, with the sample obtained by using total RNA derived from human colorectal cancer as a template, a band with a nucleotide length shorter than that derived from the reported transcription starting point was identified. From these results, it was suggested that, in the OATP1B3 mRNA derived from human colorectal cancer, different transcription starting point from that already reported (locating down-stream (3') side from the reported point) exists. In addition, "Non-template control" shown in FIG. 3 is a negative control which does not include template ("NTC" in FIG. 5 mentioned later is the same meaning).

Subsequently, after separation and purification was carried out, the DNA fragment comprising the Nested-PCR product obtained above was inserted in pTAC-1 vector using DynaExpress TA PCR Cloning Kit (BioDynamics Laboratory Inc., Tokyo, Japan), and selected using ampicillin. Plasmid DNA was refined using Plasmid Miniprep Kit (Bio-Rad Laboratories Inc.). The nucleotide sequence of the obtained plasmid DNA was subjected to a cycle-sequencing reaction using CEQ™ DTCS-Quick Start Mix (Beckman Coulter, Inc., Fullerton, Calif., USA), and analyzed using CEQ 2000 XL DNA analysis system (Beckman Coulter, Inc.), to identify the new transcription starting point of SLCO1B3 gene.

When the nucleotide sequence near the new transcription starting point of SLCO1B3 gene was compared with the database of human genomic DNA, it became evident that a novel transcription starting point exists in the region of the intron 2 of SLCO1B3 gene, and further a new exon (exon SV) exists in this region. Moreover, this exon SV has been spliced to the exon 3 of OATP1B3/wt (see FIG. 4).

6. Preparation of cDNA, and Analysis of mRNA Expression by RT-PCR Method

Figure 5:
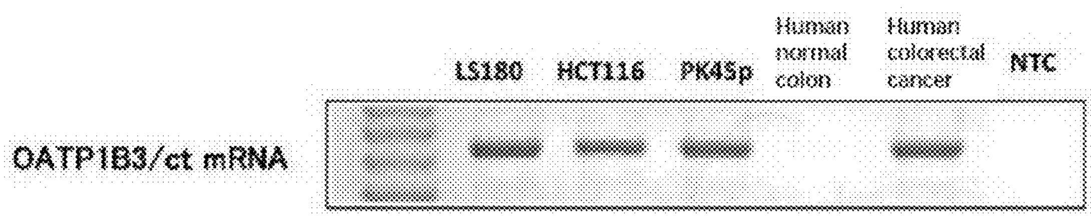
FIG. 5 is a photograph showing the results of agarose gel electrophoresis performed to visualize the results of RT-PCR carried out using the total RNA from LS180 cell, PK45p cell, human colon cancer/normal colon pair RNA and the total RNA derived from the Caucasian liver as a template in "6. Preparation of cDNA and analysis of mRNA expression by RT-PCR method" in Example.

The total RNA extracted from LS180 cell, PK45p cell by the procedure described in the above Item 4, a pair of cancerous/normal colon total RNA and the total RNA derived from the Caucasian liver were used as a template; the reverse transcriptase reaction was carried out using High Capacity cDNA Reverse transcriptase kit (Applied Biosystems Inc.); and respective cDNAs were prepared. The RT-PCR was carried out using this cDNA as a template, and the expression level of new OATP1B3 mRNA was analyzed. As for the PCR, 20 μL of PCR reaction solution containing 10 μL of GoTaq Green Master Mix, 1 μL of template cDNA, and each 0.5 μL of 10 μM forward primer and reverse primer ("SLCO1B3 TSS in cancer 33F" and "SLCO1B3 TSS in cancer 145R", as shown in the above Table 3) was prepared. After heating this reaction solution at 95° C. for 30 seconds, a reaction cycle composed of heating at 95° C. for 10 seconds, at annealing temperature suitable for respective primers ("annealing temperature", as shown in the above Table 3) for 10 seconds and at 72° C. for 15 to 20 seconds was repeated for 38 times. The PCR product was subjected to 3% agarose gel electrophoresis, and visualized by ethidium bromide staining. Results of the electrophoresis are shown in FIG. 5. As shown in FIG. 5, in addition to human colon cancer tissue, expression of novel OATP1B3 mRNA was confirmed in LS180 cell and HCT116 cell each derived from colon cancer and PK45p cell derived from pancreatic cancer, as well. On the other hand, expression of this mRNA was not identified in the normal human colon tissue. From these results, since this novel OATP1B3 mRNA was considered to be a molecular species expressed highly in cancer cell/tissue, it was named as "OATP1B3/ct".

7. cDNA Cloning of OATP1B3/ct

The cDNA cloning of OATP1B3/ct was carried out by the PCR using cDNA derived from human colorectal cancer as a template, and using a primer set (ctSLCO1B3 cloning F33 and ctSLCO1B3 cloning 2149R) shown in the above Table 4 and PrimeSTAR HS DNA polymerase (Takara Bio Inc., Shiga, Japan). In addition, as shown in Table 4, the forward primer employed for the cDNA cloning of OATP1B3/ct was identical to that of "SLCO1B3 TSS in cancer 33F" employed for the RT-PCR of the above-described "6. Preparation of cDNA, and analysis of mRNA expression by RT-PCR method". The PCR was carried out under the conditions that after heating at 94° C. for 3 minutes, 40 cycles of sequential heating at 98° C. for 10 minutes, 58° C. for 5 seconds, and 72° C. for 2 minutes and 30 seconds, and 72° C. for 3 minutes as the final step were repeated. The PCR product obtained was isolated by 1% agarose gel electrophoresis and refined by extraction, then inserted into pCR Blunt-II TOPO vector (Invitrogen Corporation). By processing the obtained construct by XbaI (Nippon Gene Co., Ltd., Tokyo, Japan) and BamHI (Nippon Gene Co., Ltd.), OATP1B3/ct cDNA was clipped, and the obtained cDNA was allowed to ligation with the similarly processed pcDNA3.1(−) Neo vector (Invitrogen Corporation), to produce OATP1B3/ct/pcDNA3.1(−).

In addition, the cDNA cloning of OATP1B3/wt was also performed by the same procedures. Specifically, the cloning was carried out by the PCR using cDNA derived from Caucasian liver as a template, and using a primer set (SLCO1B3 F27 and SLCO1B3 cloning 218R) shown in the above Table 4 and KOD-plus-Polymerase (TOYOBO Co., LTD., Osaka, Japan). The PCR reaction was carried out under the conditions that after heating at 94° C. for 3 minutes, 35 cycles of sequential heating at 94° C. for 30 minutes, 48° C. for 30 seconds, and 68° C. for 2 minutes and 30 seconds, and 68° C. for 5 minutes as the final step were repeated. The PCR product obtained was isolated by 1% agarose gel electrophoresis and refined by extraction, then inserted into pCR Blunt-II TOPO vector (Invitrogen Corporation). By processing the obtained construct by ApaI (Nippon Gene Co., Ltd.) and BamHI, OATP1B3/wt cDNA was clipped, and the obtained cDNA was allowed to ligation with the similarly processed pcDNA3.1(−) Neo vector, to produce OATP1B3/wt/pcDNA3.1(−).

Figure 4:
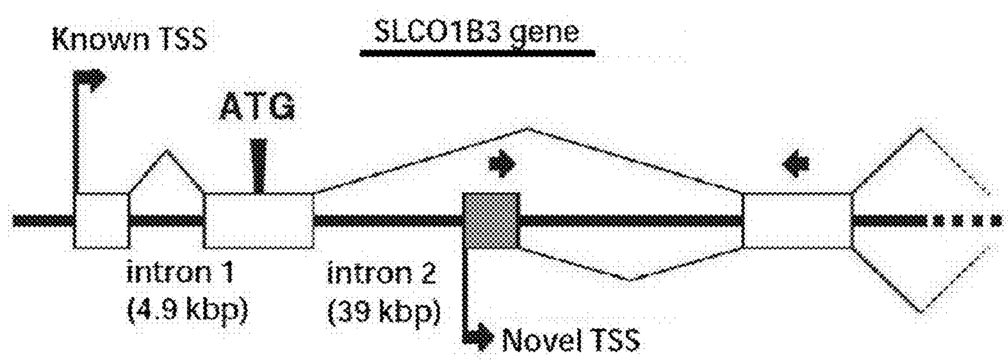
FIG. 4 is a diagram showing the structure of human SLCO1B3 gene.

The nucleotide sequences of OATP1B3/ct and OATP1B3/wt in two plasmids prepared as described above were analyzed using CEQ 2000 Dye terminator Cycle Sequencing with Quick Start Kit (Beckman Coulter, Inc.) and CEQ 2000 XL DNA analysis system (Beckman Coulter, Inc.). In FIG. 1, cDNA sequence of OATP1B3/ct (SEQ ID NO: 1) measured herewith is shown together with the cDNA sequence of OATP1B3/wt (Refseq Accession No. NM_019844, SEQ ID NO: 2). In addition, as shown in FIGS. 1 and 4, it can be confirmed that, in OATP1B3/ct, the exon 1 and exon 2 of OATP1B3/wt are deleted, and instead, exon SV exists and splicing to the exon 3 of OATP1B3/wt.

8. Analysis of mRNA Expression by Quantitative Real-Time PCR

Using GHL pool (cDNA pool prepared from five Japanese liver samples) which was prepared by the procedure described in the above item 6, HHL pool (cDNA pool prepared from five Caucasian live samples), cDNA derived from each human colorectal cancer tissue, LS180 cell, K45p cell, and HCT116 cell, and using plasmid prepared according to the procedure described in the above item 7, quantitative real-time PCR was performed, and quantitative measurement of each mRNA of OATP1B3/ct and OATP1B3/wt was carried out using standard curve method. For the detection of PCR and DNA amplification, ABI PRISM® 7000 (Applied Biosystems Inc.) was employed.

For the detection of OATP1B3/ct mRNA, a 20 μL of PCR reaction solution containing 1 μL of template cDNA, 10 μL of 2× FastStart Universal Probe Master (ROX) (Roche Diagnostics, GmbH, Penzberg, Germany), 0.2 μL of Universal Probe #59 (Roche Diagnostics, GmbH), and each 0.4 μL of a primer set (ctSLCO1B3 Left 59-76, and ctSLCO1B3 Right 130-151) shown in the above Table 5 was prepared. The detection was performed by 2-step PCR in which, after heating the reaction solution at 95° C. for 5 minutes, the cycle of heating at 95° C. for 15 seconds and at 60° C. for 1 minute was repeated for 45 times.

On the other hand, for the detection of OATP1B3/wt mRNA, a 20 μL of PCR reaction solution containing 1 μL of template cDNA, 10 μL of 2×SYBER Premix Ex Taq II (Takara Bio Inc.), 0.4 μL of 50×ROX Reference Dye (Takara Bio Inc.), and each 0.8 μL of a primer set (SLCO1B3 F153 for real-time, and SLCO1B3 R194 for real-time) shown in the above Table 5 was prepared. The detection was performed by 2-step PCR in which, after heating the reaction solution at 95° C. for 20 seconds, the cycle of heating at 95° C. for 5 seconds and at 60° C. for 33 seconds was repeated for 40 times.

As to the sample for standard curve, the sample for the measurement of OATP1B3/ct mRNA was prepared by using OATP1B3/pTOPO prepared by the procedure described in the above item 7. as a template, and using 5 points in a range of $2.86\times10^{-23}$ to $1.43\times10^{-17}$ mole per well; on the other hand, the sample for the measurement of OATP1B3/wt mRNA was prepared by using OATP1B3/pcDNA3.1(−) prepared by the procedure described in the above item 7. as a template, and using 5 points in a range of $1.09\times10^{-23}$ to $1.09\times10^{-17}$ mole per well. Detection of PCR and DNA amplification was performed as in the case with the cDNA samples. Moreover, the standard curve was obtained by linear regression based on the least-squares method.

Figure 6:
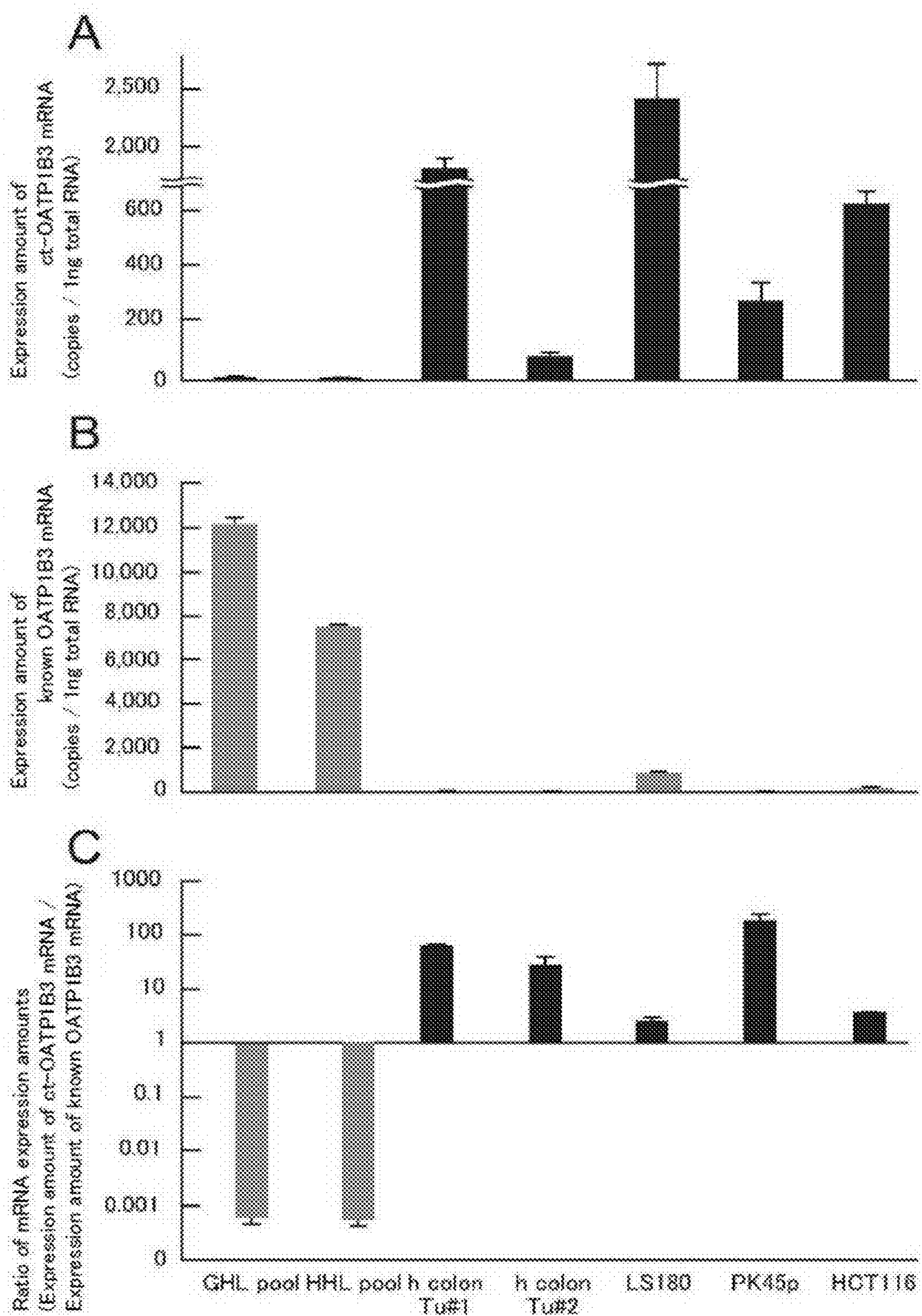
FIG. 6 is a graph which shows the results (mRNA expression profiles) of "8. Analysis mRNA expression by quantitative real-time PCR" in Example.

The mRNA expression profiles obtained as a result of the real time quantitative PCR is shown in FIG. 6. FIG. 6-A shows expression levels of OATP1B3/ct in respective tissues and cells. Also, FIG. 6-B shows expression levels of OATP1B3/wt in respective tissues and cells. In addition, the bar shown in FIG. 6 represents number of copies of OATP1B3 mRNA as average value±standard deviation in three independent experiments. Furthermore, FIG. 6-C shows ratio of expression level (copy number of OATP1B3/ct versus copy number of OATP1B3/wt).

As shown in FIG. 6-A, copy number of OATP1B3/ct mRNA present in 1 ng of total RNA was 8 for the GHL pool (Japanese liver), and it was 4 for the HHL pool (Caucasian liver). In contrast, in human colorectal cancer tissue, h colon Tu #1 and #2, it was 1812 and 89, respectively, and 2411 for LS180 cell, 289 for PK45p cell, and 644 for HCT116 cell. On the other hand, copy number of OATP1B3/wt mRNA was 12187 for GHL pool and 7473 for HHL pool, and in human colorectal cancer tissue, h colon Tu #1 and #2, it was 30 and 3, respectively, and 865 for LS180 cell, 2 for PK45p cell, and 172 for HCT116 cell. Therefore, the amount of OATP1B3/ct mRNA expression was, in comparison with the amount of OATP1B3/wt mRNA expression, 60 times and 30 times higher in human colorectal cancer tissue h colon Tu #1 and #2, respectively, 2.8 times higher in LS180 cell, 144.5 times higher in PK45p cell, and 3.7 times higher in HCT116 cell (FIG. 6-C). On the other hand, in GHL pool and HHL pool, the amount of expression of OATP1B3/ct mRNA was about 1/1500 and about 1/1700 of the amount of expression of OATP1B3/wt mRNA, respectively. From the results obtained above, it was shown that OATP1B3/ct mRNA was almost specifically expressed in human colorectal cancer tissue, and in addition, in the cells derived from human colorectal cancer also expressed OATP1B3/ct mRNA very dominantly. That is, by the inventors of the present application, it was clarified that what was expressed in cancer cell and tissue was not the previously reported OATP1B3/wt, but an alternative splicing variant which was newly discovered this time.

9. Preparation of Expression Plasmid for Green Fluorescent Protein (GFP) Fusion ctOATP1B3 Peptide As shown in FIG. 7, a putative open reading frame (ORF) is present in each frame of OATP1B3/ct mRNA. It is presumed that two ORFs of frame 1 (f1-1 and f1-2) encode a peptide which consists of 10 amino acids and a peptide which consists of 27 amino acids, respectively. In addition, it was presumed that ORF of frame 2 encodes a protein consisting of 655 amino acids, which uses the midway of the frame of OATP1B3/wt as an initiation codon and share as it is as a stop codon of OATP1B3/wt (f2). Further, it was presumed that the ORF of frame 3 encodes the peptide which consists of 43 amino acids (f3). To analyze expression of these translation product, the plasmid which expresses GFP-fused protein (f1-1/GFP, f1-2/GFP, f2/GFP, f3/GFP) on each C-terminal side of the peptide coding region (f1-1, f1-2, f3) which exists in the frame 1 and frame 3 of OATP1B3/ct mRNA, and on the C-terminal side of N-terminal 20 amino acid region of the protein coding region (f2) was prepared.

Using OATP1B3/ct/pcDNA3.1(−) as a template, and using a primer shown in Table 6, F1-2 region, f2 region, and f3 region were amplified by PCR (after 95° C. for 30 seconds, a cycle of 95° C. for 10 seconds, 60° C. for 10 seconds, and 72° C. for 20 seconds was repeated 40 times, and 72° C. for 10 seconds was the final step). In addition, as to GFP and f1-1/GFP, using primer shown in Table 6, and using pAcGFP-c1 as a template, amplification was carried out by PCR (after heating at 94° C. for 3 minutes, a cycle of 98° C. for 10 seconds, 59° C. for 5 seconds, and 72° C. for 50 seconds was repeated 40 times, and 72° C. for 3 minutes was the final step). The PCR product of GFP was processed with BamHI, and then ligation was carried out with each similarly BamHI-processed PCR product of f1-2, f2 and f3. Using them as a template, and using the primer shown in Table 6, amplification was performed by the PCR (after heating at 94° C. for 2 minutes, a cycle of 94° C. for 10 seconds, 60° C. for 30 seconds, and 72° C. for 60 seconds was repeated 35 times, and 72° C. for 30 seconds was the final step). Each of f1-2/GFP and f3/GFP obtained was inserted in pTAC-1 vector using DynaExpress TA PCR Cloning Kit (BioDynamics Laboratory Inc., Tokyo, Japan). Also, each of f1-1/GFP and f2/GFP obtained was inserted in pCR Blunt-II TOPO vector (Invitrogen Corporation). These plasmids were processed with XbaI and KpnI, and then ligation was carried out with similarly processed pcDNA3.1 (−)Neo, to produce f1-1/GFP/pcDNA3.1, f1-2/GFP/pcDNA3.1, f2/GFP/pcDNA3.1, and f3/GFP/pcDNA3.1.

10. Reverse Transfection

Figure 8:
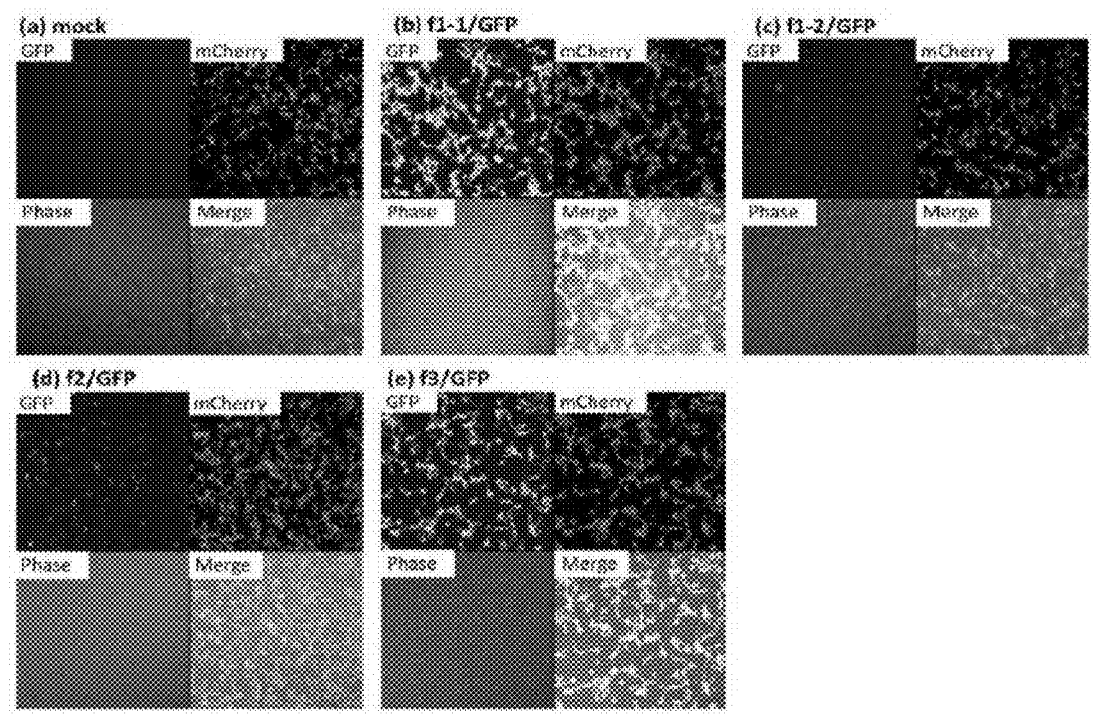
FIG. 8 is a graph showing the results of "10. Reverse transfection" in Example. In addition, green color is the fluorescence derived from the GFP; and red color is the fluorescence derived from the mCherry which serves as a transfection control. Also, a superposition of both fluorescences is shown as Merge, and a differential interference image is shown as Phase.

To a mixture of 320 ng/well of mCherry/pcDNA3.1(−) and 320 ng/well of each GFP fusion peptide expression plasmid or empty pcDNA3.1(−)Neo (mock), 100 μL/well of OPTI-MEM® (Invitrogen Corporation) and 0.5 μL/well of Plus Reagent (Invitrogen Corporation) were mixed, and 1.6 μL/well of Lipofectamin LTX (Invitrogen Corporation) was added thereto, and together with this, $3.5\times10^5$ cell/well of 293FT cell was seeded to 24 well plate. The green fluorescence of the GFP origin and the red fluorescence of the mCherry origin were observed after 24 hours from seeding using Olympus Fluoview ver2.3 (Olympus Corporation, Tokyo, Japan). Results are shown in FIG. 8. Here, in FIG. 8, green color is the fluorescence of the GFP origin and red color is the fluorescence of the mCherry origin which is transfection control. Moreover, superposition of both fluorescences is shown as Merge and a differential interference image is shown as Phase. In addition, all laser intensity and exposure time employed for analysis were made equal.

As shown in FIG. 8, the strong fluorescence was observed in the transfected 293FT cell which is considered to be f1-1/GFP and f3/GFP origin (FIGS. 8 (*b*) and (*e*)). In addition, the fluorescence of f2/GFP origin was also observed (FIG. 8 (*d*)). On the other hand, very weak fluorescence was observed from f1-2/GFP (FIG. 8 (*c*)). In addition, green fluorescence was not observed in the experiment using mock performed simultaneously (FIG. 8 (*a*)). In addition, in either experiment, the red fluorescence of mCherry origin showed the equivalent coloring level.

[Sequence Listing Free Text]

[SEQ ID NO: 1]

This shows the nucleotide sequence of cDNA of OATP1B3/ct.

[SEQ ID NO: 2]

This shows the nucleotide sequence of cDNA of OATP1B3/wt.

[SEQ ID NO: 3]

This shows the amino acid sequence of the protein which is coded by OATP1B3/wt.

[SEQ ID NO: 4]

This shows the nucleotide sequence of the frame 1-1 (including stop codon) of OATP1B3/ct.

[SEQ ID NO: 5]

This shows the amino acid sequence of the peptide (f1-1) which is coded by the frame 1-1 of OATP1B3/ct.

[SEQ ID NO: 6]

This shows the nucleotide sequence of the frame 1-2 (including stop codon) of OATP1B3/ct.

[SEQ ID NO: 7]

This shows the amino acid sequence of the peptide (f1-2) which is coded by the frame 1-2 of OATP1B3/ct.

[SEQ ID NO: 8]

This shows the nucleotide sequence of the frame 2 (including stop codon) of OATP1B3/ct.

[SEQ ID NO: 9]

This shows the amino acid sequence of the peptide (f2) which is coded by the frame 2 of OATP1B3/ct.

[SEQ ID NO: 10]

This shows the nucleotide sequence of the frame 3 (including stop codon) of OATP1B3/ct.

[SEQ ID NO: 11]

This shows the amino acid sequence of the peptide (f3) which is coded by the frame 3 of OATP1B3/ct.

[SEQ ID NO: 12]

This shows the nucleotide sequence of the forward primer used for amplification of a human GAPDH gene.

[SEQ ID NO: 13]

This shows the nucleotide sequence of the reverse primer used for amplification of a human GAPDH gene.

[SEQ ID NO: 14]

This shows the nucleotide sequence of the reverse primer used for the Touch-down PCR in RLM-5'-RACE.

[SEQ ID NO: 15]

This shows the nucleotide sequence of the reverse primer used for the Nested-PCR in RLM-5'-RACE.

[SEQ ID NO: 16]

This shows the nucleotide sequence of the forward primer used for the RT-PCR and the cDNA cloning of OATP1B3/ct.

[SEQ ID NO: 17]

This shows the nucleotide sequence of the reverse primer used for the RT-PCR.

[SEQ ID NO: 18]

This shows the nucleotide sequence of the reverse primer used for the cDNA cloning of OATP1B3/ct.

[SEQ ID NO: 19]

This shows the nucleotide sequence of the forward primer used for the cDNA cloning of OATP1B3/wt.

[SEQ ID NO: 20]

This shows the nucleotide sequence of the reverse primer used for the cDNA cloning of OATP1B3/wt.

[SEQ ID NO: 21]

This shows the nucleotide sequence of the forward primer used for the detection of OATP1B3/ct in the quantitative real-time PCR.

[SEQ ID NO: 22]

This shows the nucleotide sequence of the reverse primer used for the detection of OATP1B3/ct in the quantitative real-time PCR.

[SEQ ID NO: 23]

This shows the nucleotide sequence of the forward primer used for the detection of OATP1B3/wt in the quantitative real-time PCR.

[SEQ ID NO: 24]

This shows the nucleotide sequence of the reverse primer used for the detection of OATP1B3/wt in the quantitative real-time PCR.

[SEQ ID NO: 25]

This shows the nucleotide sequence of the forward primer used for the expression of the peptide consisting of the amino acid sequence from f1-1/GFP/pcDNA3.1 of SEQ ID NO: 5.

[SEQ ID NO: 26]

This shows the nucleotide sequence of the reverse primer used for the expression of the peptide consisting of amino acid sequence from f1-1/GFP/pcDNA3.1 of SEQ ID NO: 5.

[SEQ ID NO: 27]

This shows the nucleotide sequence of the forward primer used for the expression of a peptide consisting of the amino acid sequence from f1-2/GFP/pcDNA3.1 of SEQ ID NO: 7, for the expression of a protein consisting of the amino acid sequence from f2/GFP/pcDNA3.1 of SEQ ID NO: 9, and for the expression of a peptide consisting of the amino acid sequence from f3/GFP/pcDNA3.1 of SEQ ID NO: 11.

[SEQ ID NO: 28]

This shows the nucleotide sequence of the reverse primer used for the expression of a peptide consisting of the amino acid sequence from f1-2/GFP/pcDNA3.1 of SEQ ID NO: 7.

[SEQ ID NO: 29]

This shows the nucleotide sequence of the reverse primer used for the expression of a protein consisting of the amino acid sequence from f2/GFP/pcDNA3.1 of SEQ ID NO: 9.

[SEQ ID NO: 30]

This shows the nucleotide sequence of the reverse primer used for the expression of a peptide consisting of the amino acid sequence from f3/GFP/pcDNA3.1 of SEQ ID NO: 11.

[SEQ ID NO: 31]

This shows the nucleotide sequence of the forward primer used for the expression of GFP protein from f1-1/GFP/pcDNA3.1, f1-2/GFP/pcDNA3.1, f2/GFP/pcDNA3.1, and f3/GFP/pcDNA3.1.

[SEQ ID NO: 32]

This shows the nucleotide sequence of the reverse primer used for the expression of GFP protein from f1-1/GFP/pcDNA3.1, f1-2/GFP/pcDNA3.1, f2/GFP/pcDNA3.1, and f3/GFP/pcDNA3.1.

The invention claimed is:

1. A method for screening a therapeutic agent for human colon cancer or human pancreatic cancer, the method comprising:

culturing cancer cells in the presence of a test substance and, separately, in the absence of the test substance, measuring in the cancer cells cultured in the presence of the test substance and in the cancer cells cultured in the absence of the test substance an amount of an alternative splicing variant of Organic Anion Transporting Polypeptide 1B3 (OATP1B3) mRNA that contains exon SV, and comparing the amount of the alternative splicing variant of OATP1B3 mRNA in the cancer cells cultured in the presence of the test substance to the amount of the alternative splicing variant of OATP1B3 mRNA in the cancer cells cultured in the absence of the test substance, wherein the test substance is effective as a therapeutic agent for cancer if the amount of the alternative splicing variant of OATP1B3 mRNA measured in the cancer cells in the presence of the test substance is decreased as compared to the amount of the alternative splicing variant of OATP1B3 mRNA in the cancer cells cultured in the absence of the test substance, the cancer cells are human colon cancer cells or human pancreatic cancer cells, wherein the measuring step is carried out by amplification via an RT-PCR assay of an mRNA comprising SEQ ID NO: 1, whereby the RT-PCR assay does not amplify an mRNA comprising SEQ ID NO: 2, and the RT-PCR assay detects the presence of exon SV in SEQ ID NO: 1 by specifically amplifying mRNA comprising SEQ ID NO: 1 or a partial region of cDNA thereof using a primer in exon SV and measuring the amplification product.

2. The method of claim 1, wherein the primer is 15 to 35 nucleotides in length.

3. The method of claim 1, wherein the amplification product is measured by real-time PCR.

4. The method of claim 1, wherein the amplification product is measured by detecting fluorescent bands after electrophoresis of the amplification product.

5. The method of claim 1, wherein the amplification product is measured by Southern blot analysis.

6. The method of claim 3, wherein the primer is 15 to 35 nucleotides in length.

* * * * *